US008690939B2

(12) United States Patent
Miller et al.

(10) Patent No.: US 8,690,939 B2
(45) Date of Patent: Apr. 8, 2014

(54) METHOD FOR GUIDE-WIRE BASED ADVANCEMENT OF A ROTATION ASSEMBLY

(75) Inventors: Eran Miller, Moshav Beit Elazari (IL); Oz Cabiri, Macabim-Reut (IL)

(73) Assignee: Valtech Cardio, Ltd., Or Yehuda (IL)

( * ) Notice: Subject to any disclaimer, the term of this patent is extended or adjusted under 35 U.S.C. 154(b) by 615 days.

(21) Appl. No.: 12/795,192

(22) Filed: Jun. 7, 2010

(65) Prior Publication Data

US 2011/0301698 A1   Dec. 8, 2011

(51) Int. Cl.
*A61F 2/24* (2006.01)

(52) U.S. Cl.
USPC ........................................................ 623/2.11

(58) Field of Classification Search
USPC .......... 623/2.1, 2.11, 2.36; 128/898; 606/139, 606/144, 145, 228
See application file for complete search history.

(56) References Cited

U.S. PATENT DOCUMENTS

| | | |
|---|---|---|
| 4,602,911 A | 7/1986 | Ahmadi et al. |
| 4,625,727 A | 12/1986 | Leiboff |
| 4,778,468 A | 10/1988 | Hunt et al. |
| 4,917,698 A | 4/1990 | Carpentier et al. |
| 5,061,277 A | 10/1991 | Carpentier et al. |
| 5,104,407 A | 4/1992 | Lam et al. |
| 5,108,420 A | 4/1992 | Marks |
| 5,306,296 A | 4/1994 | Wright et al. |
| 5,450,860 A | 9/1995 | O'Connor |
| 5,477,856 A | 12/1995 | Lundquist |
| 5,601,572 A | 2/1997 | Middleman et al. |
| 5,669,919 A | 9/1997 | Sanders et al. |
| 5,674,279 A | 10/1997 | Wright et al. |
| 5,810,882 A | 9/1998 | Bolduc |
| 5,824,066 A | 10/1998 | Gross |
| 5,843,120 A | 12/1998 | Israel et al. |
| 5,876,373 A | 3/1999 | Giba et al. |
| 5,961,440 A | 10/1999 | Schweich et al. |

(Continued)

FOREIGN PATENT DOCUMENTS

| | | |
|---|---|---|
| WO | 92/05093 | 4/1992 |
| WO | WO 01/26586 | 4/2001 |

(Continued)

OTHER PUBLICATIONS

Dictionary.com definition of "lock".*

(Continued)

*Primary Examiner* — Ryan Severson
*Assistant Examiner* — Katherine M Shi
(74) *Attorney, Agent, or Firm* — Sughrue Mion, PLLC

(57) ABSTRACT

A method is provided including coupling a tissue-engaging element to a first portion of cardiac tissue of a heart of a patient and advancing toward the tissue-engaging element an adjustment mechanism along at least one guide member that is removably coupled to the tissue-engaging element. The adjustment mechanism engages a first portion of a first flexible longitudinal member. A second portion of the first flexible longitudinal member is coupled to a second portion of cardiac tissue. Following the coupling of the second portion of the first flexible longitudinal member to the second portion of cardiac tissue, the adjustment mechanism is slid further along the guide member and coupled to the tissue-engaging element. Using the adjustment mechanism, a length of the first flexible longitudinal member is adjusted between the first and second portions of cardiac tissue. Other applications are also described.

39 Claims, 15 Drawing Sheets

(56) References Cited

U.S. PATENT DOCUMENTS

| | | | |
|---|---|---|---|
| 5,961,539 | A | 10/1999 | Northrup, III et al. |
| 6,045,497 | A | 4/2000 | Schweich et al. |
| 6,050,936 | A | 4/2000 | Schweich et al. |
| 6,059,715 | A | 5/2000 | Schweich et al. |
| 6,165,119 | A | 12/2000 | Schweich et al. |
| 6,251,092 | B1 | 6/2001 | Qin et al. |
| 6,315,784 | B1 | 11/2001 | Djurovic |
| 6,319,281 | B1 | 11/2001 | Patel |
| 6,332,893 | B1 | 12/2001 | Mortier et al. |
| 6,406,420 | B1 | 6/2002 | McCarthy et al. |
| 6,451,054 | B1 | 9/2002 | Stevens |
| 6,524,338 | B1 | 2/2003 | Gundry |
| 6,537,314 | B2 | 3/2003 | Langberg et al. |
| 6,554,845 | B1 | 4/2003 | Fleenor et al. |
| 6,564,805 | B2 | 5/2003 | Garrison et al. |
| 6,569,198 | B1 | 5/2003 | Wilson et al. |
| 6,589,160 | B2 | 7/2003 | Schweich et al. |
| 6,602,288 | B1 | 8/2003 | Cosgrove |
| 6,602,289 | B1 | 8/2003 | Colvin et al. |
| 6,613,078 | B1 | 9/2003 | Barone |
| 6,613,079 | B1 | 9/2003 | Wolinsky et al. |
| 6,619,291 | B2 | 9/2003 | Hlavka et al. |
| 6,626,899 | B2 | 9/2003 | Houser et al. |
| 6,626,930 | B1 | 9/2003 | Allen et al. |
| 6,629,534 | B1 | 10/2003 | St. Goar et al. |
| 6,629,921 | B1 | 10/2003 | Schweich et al. |
| 6,651,671 | B1 | 11/2003 | Donlon et al. |
| 6,682,558 | B2 | 1/2004 | Tu et al. |
| 6,689,164 | B1 | 2/2004 | Seguin |
| 6,695,866 | B1 | 2/2004 | Kuehn et al. |
| 6,702,826 | B2 | 3/2004 | Liddicoat et al. |
| 6,702,846 | B2 | 3/2004 | Mikus et al. |
| 6,718,985 | B2 | 4/2004 | Hlavka et al. |
| 6,723,038 | B1 | 4/2004 | Schroeder et al. |
| 6,726,717 | B2 | 4/2004 | Alfieri et al. |
| 6,749,630 | B2 | 6/2004 | McCarthy et al. |
| 6,752,813 | B2 | 6/2004 | Goldfarb et al. |
| 6,764,510 | B2 | 7/2004 | Vidlund et al. |
| 6,786,924 | B2 | 9/2004 | Ryan et al. |
| 6,802,319 | B2 | 10/2004 | Stevens et al. |
| 6,805,710 | B2 | 10/2004 | Bolling et al. |
| 6,858,039 | B2 | 2/2005 | McCarthy |
| 6,884,250 | B2 | 4/2005 | Monassevitch et al. |
| 6,893,459 | B1 | 5/2005 | Macoviak |
| 6,908,482 | B2 | 6/2005 | McCarthy et al. |
| 6,960,217 | B2 | 11/2005 | Bolduc |
| 6,986,775 | B2 | 1/2006 | Morales et al. |
| 6,989,028 | B2 | 1/2006 | Lashinski |
| 7,004,176 | B2 | 2/2006 | Lau |
| 7,011,669 | B2 | 3/2006 | Kimblad |
| 7,011,682 | B2 | 3/2006 | Lashinski |
| 7,037,334 | B1 | 5/2006 | Hlavka et al. |
| 7,087,064 | B1 | 8/2006 | Hyde |
| 7,101,395 | B2 | 9/2006 | Tremulis et al. |
| 7,112,207 | B2 | 9/2006 | Allen et al. |
| 7,125,421 | B2 | 10/2006 | Tremulis et al. |
| 7,159,593 | B2 | 1/2007 | McCarthy |
| 7,169,187 | B2 | 1/2007 | Datta et al. |
| 7,175,660 | B2 | 2/2007 | Cartledge et al. |
| 7,186,262 | B2 | 3/2007 | Saadat |
| 7,189,199 | B2 | 3/2007 | McCarthy et al. |
| 7,226,467 | B2 | 6/2007 | Lucatero et al. |
| 7,238,191 | B2 | 7/2007 | Bachmann |
| 7,294,148 | B2 | 11/2007 | McCarthy |
| 7,297,150 | B2 | 11/2007 | Cartledge et al. |
| 7,311,728 | B2 | 12/2007 | Solem et al. |
| 7,316,710 | B1 | 1/2008 | Cheng et al. |
| 7,329,280 | B2 | 2/2008 | Bolling et al. |
| 7,390,329 | B2 | 6/2008 | Westra et al. |
| 7,404,824 | B1 | 7/2008 | Webler et al. |
| 7,431,692 | B2 | 10/2008 | Zollinger et al. |
| 7,452,376 | B2 | 11/2008 | Lim et al. |
| 7,455,690 | B2 | 11/2008 | Cartledge et al. |
| 7,507,252 | B2 | 3/2009 | Lashinski et al. |
| 7,530,995 | B2 | 5/2009 | Quijano |
| 7,549,983 | B2 | 6/2009 | Roue et al. |
| 7,563,267 | B2 | 7/2009 | Goldfarb et al. |
| 7,563,273 | B2 | 7/2009 | Goldfarb et al. |
| 7,569,062 | B1 | 8/2009 | Kuehn |
| 7,588,582 | B2 | 9/2009 | Starksen et al. |
| 7,604,646 | B2 | 10/2009 | Goldfarb et al. |
| 7,608,091 | B2 | 10/2009 | Goldfarb et al. |
| 7,608,103 | B2 | 10/2009 | McCarthy |
| 7,618,449 | B2 | 11/2009 | Tremulis et al. |
| 7,632,303 | B1 | 12/2009 | Stalker et al. |
| 7,635,329 | B2 | 12/2009 | Goldfarb et al. |
| 7,635,386 | B1 | 12/2009 | Gammie |
| 7,655,015 | B2 | 2/2010 | Goldfarb et al. |
| 7,871,433 | B2 | 1/2011 | Lattouf |
| 7,993,368 | B2 | 8/2011 | Gambale et al. |
| 8,070,804 | B2 | 12/2011 | Hyde |
| 8,142,495 | B2 | 3/2012 | Hasenkam |
| 2001/0021874 | A1 | 9/2001 | Carpentier |
| 2002/0087048 | A1 | 7/2002 | Brock et al. |
| 2002/0103532 | A1 | 8/2002 | Langberg et al. |
| 2002/0173841 | A1 | 11/2002 | Ortiz et al. |
| 2002/0177904 | A1 | 11/2002 | Huxel et al. |
| 2003/0050693 | A1 | 3/2003 | Quijano et al. |
| 2003/0105519 | A1 | 6/2003 | Fasol et al. |
| 2003/0167062 | A1 | 9/2003 | Gambale et al. |
| 2003/0229350 | A1 | 12/2003 | Kay |
| 2003/0233142 | A1 | 12/2003 | Morales et al. |
| 2004/0024451 | A1 | 2/2004 | Johnson et al. |
| 2004/0122514 | A1 | 6/2004 | Fogarty et al. |
| 2004/0138744 | A1 | 7/2004 | Lashinski et al. |
| 2004/0148021 | A1 | 7/2004 | Cartledge et al. |
| 2004/0172046 | A1 | 9/2004 | Hlavka |
| 2004/0181287 | A1 | 9/2004 | Gellman |
| 2004/0186566 | A1 | 9/2004 | Hindrichs |
| 2004/0236419 | A1 | 11/2004 | Milo |
| 2005/0004668 | A1 | 1/2005 | Aklog et al. |
| 2005/0016560 | A1 | 1/2005 | Voughlohn |
| 2005/0055087 | A1 | 3/2005 | Starksen |
| 2005/0060030 | A1 | 3/2005 | Lashinski et al. |
| 2005/0065601 | A1 | 3/2005 | Lee et al. |
| 2005/0090827 | A1 | 4/2005 | Gedebou |
| 2005/0107871 | A1 | 5/2005 | Realyvasquez et al. |
| 2005/0125011 | A1 | 6/2005 | Spence et al. |
| 2005/0171601 | A1 | 8/2005 | Cosgrove |
| 2005/0177228 | A1 | 8/2005 | Solem et al. |
| 2005/0203549 | A1 | 9/2005 | Realyvasquez |
| 2005/0203606 | A1 | 9/2005 | VanCamp |
| 2005/0216039 | A1 | 9/2005 | Lederman |
| 2005/0288781 | A1 | 12/2005 | Moaddeb et al. |
| 2006/0025787 | A1 | 2/2006 | Morales et al. |
| 2006/0041319 | A1 | 2/2006 | Taylor et al. |
| 2006/0069429 | A1 | 3/2006 | Spence et al. |
| 2006/0085012 | A1 | 4/2006 | Dolan |
| 2006/0129166 | A1 | 6/2006 | Lavelle |
| 2006/0161265 | A1 | 7/2006 | Levine et al. |
| 2006/0241656 | A1 | 10/2006 | Starksen et al. |
| 2006/0241748 | A1 | 10/2006 | Lee et al. |
| 2006/0282161 | A1 | 12/2006 | Huynh et al. |
| 2006/0287716 | A1 | 12/2006 | Banbury |
| 2007/0016287 | A1 | 1/2007 | Cartledge et al. |
| 2007/0027536 | A1 | 2/2007 | Mihaljevic et al. |
| 2007/0049942 | A1 | 3/2007 | Hindrichs et al. |
| 2007/0049970 | A1 | 3/2007 | Belef et al. |
| 2007/0051377 | A1 | 3/2007 | Douk et al. |
| 2007/0055206 | A1 | 3/2007 | To et al. |
| 2007/0080188 | A1 | 4/2007 | Spence et al. |
| 2007/0112422 | A1 | 5/2007 | Dehdashtian |
| 2007/0118151 | A1 | 5/2007 | Davidson |
| 2007/0162111 | A1 | 7/2007 | Fukamachi et al. |
| 2007/0198082 | A1 | 8/2007 | Kapadia et al. |
| 2007/0213582 | A1 | 9/2007 | Zollinger et al. |
| 2007/0219558 | A1 | 9/2007 | Deutsch |
| 2007/0239208 | A1 | 10/2007 | Crawford |
| 2007/0244556 | A1 | 10/2007 | Rafiee et al. |
| 2007/0250160 | A1 | 10/2007 | Rafiee |
| 2007/0255397 | A1 | 11/2007 | Ryan et al. |
| 2007/0255400 | A1 | 11/2007 | Parravicini et al. |
| 2007/0282375 | A1 | 12/2007 | Hindrichs et al. |
| 2008/0004697 | A1 | 1/2008 | Lichtenstein et al. |

(56) References Cited

U.S. PATENT DOCUMENTS

| | | |
|---|---|---|
| 2008/0027483 A1 | 1/2008 | Cartledge |
| 2008/0035160 A1 | 2/2008 | Woodson et al. |
| 2008/0058595 A1 | 3/2008 | Snoke et al. |
| 2008/0086203 A1 | 4/2008 | Roberts |
| 2008/0140116 A1 | 6/2008 | Bonutti |
| 2008/0262609 A1 | 10/2008 | Gross et al. |
| 2008/0288044 A1 | 11/2008 | Osborne |
| 2009/0043153 A1 | 2/2009 | Zollinger et al. |
| 2009/0105816 A1 | 4/2009 | Olsen et al. |
| 2009/0171439 A1 | 7/2009 | Nissl |
| 2009/0177266 A1 | 7/2009 | Powell et al. |
| 2009/0299409 A1 | 12/2009 | Coe et al. |
| 2009/0326648 A1 | 12/2009 | Machold et al. |
| 2010/0023117 A1 | 1/2010 | Yoganathan |
| 2010/0023118 A1 | 1/2010 | Medlock et al. |
| 2010/0042147 A1 | 2/2010 | Janovsky et al. |
| 2010/0076499 A1 | 3/2010 | McNamara et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0174358 A1 | 7/2010 | Rabkin et al. |
| 2010/0179574 A1 | 7/2010 | Longoria |
| 2010/0211166 A1 | 8/2010 | Miller et al. |
| 2010/0234935 A1 | 9/2010 | Bashiri et al. |
| 2010/0280603 A1 | 11/2010 | Maisano et al. |
| 2010/0286767 A1 | 11/2010 | Zipory |
| 2010/0324598 A1 | 12/2010 | Anderson |
| 2011/0011917 A1 | 1/2011 | Loulmet |
| 2011/0029066 A1 | 2/2011 | Gilad |
| 2011/0082538 A1 | 4/2011 | Dahlgren et al. |
| 2011/0093002 A1 | 4/2011 | Rucker et al. |
| 2011/0106245 A1 | 5/2011 | Miller et al. |
| 2011/0106247 A1 | 5/2011 | Miller |
| 2011/0184510 A1 | 7/2011 | Maisano et al. |
| 2011/0264208 A1 | 10/2011 | Duffy |

FOREIGN PATENT DOCUMENTS

| | | |
|---|---|---|
| WO | WO 02/085251 | 10/2002 |
| WO | WO 02/085252 | 10/2002 |
| WO | 2005/021063 | 3/2005 |
| WO | WO 2006/097931 | 3/2006 |
| WO | WO 2006/116558 | 11/2006 |
| WO | WO 2007/136783 | 11/2007 |
| WO | WO 2008/068756 | 6/2008 |
| WO | 2010/004546 | 1/2010 |
| WO | WO 2010/073246 | 7/2010 |
| WO | 2010/128502 | 11/2010 |
| WO | 2010/128503 | 11/2010 |
| WO | 2011/051942 | 5/2011 |
| WO | 2011/089601 | 7/2011 |

OTHER PUBLICATIONS

An Office Action dated Aug. 24, 2012, which issued during the prosecution of U.S. Appl. No. 12/563,930.
An Office Action dated May 10, 2012, which issued during the prosecution of U.S. Appl. No. 12/795,026.
A Notice of Allowance dated Jun. 26, 2012, which issued during the prosecution of U.S. Appl. No. 12/608,316.
A Supplementary European Search Report dated Feb. 1, 2011, which issued during the prosecution of Applicant's European Patent Application No. EP 07849540.
An Office Action dated Jan. 23, 2012, which issued during the prosecution of U.S. Appl. No. 12/692,061.
An International Search Report dated May 19, 2011, which issued during the prosecution of Applicant's PCT/IL2011/00064.
An Office Action dated Aug. 6, 2012, which issued during the prosecution of U.S. Appl. No. 12/548,991.
An Office Action dated Jul. 20, 2012, which issued during the prosecution of U.S. Appl. No. 12/843,412.
O'Reilly S et al., "Heart valve surgery pushes the envelope," Medtech Insight 8(3): 73, 99-108 (2006).
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Swain CP et al., "An endoscopically deliverable tissue-transfixing device for securing biosensors in the gastrointestinal tract," Gastrointestinal Endoscopy 40(6): 730-734 (1994).
Odell JA et al., "Early Results of a Simplified Method of Mitral Valve Annuloplasty," Circulation 92:150-154 (1995).
An International Search Report dated Sep. 8, 2009, which issued during the prosecution of Applicant's PCT/IL09/00593.
U.S. Appl. No. 60/873,075, filed Dec. 5, 2006.
Alfieri O. et al. Novel Suture Device for Beating-Heart Mitral leaflet Approximation. Ann Thorac Surg. 2002;74: 1488-1493.
U.S. Appl. No. 60/902,146, filed Feb. 16, 2007.
An Office Action dated Aug. 2, 2011 which issued during the prosecution of U.S. Appl. No. 12/435,291.
U.S. Appl. No. 61/001,013, filed Oct. 29, 2007.
U.S. Appl. No. 61/132,295, filed Jun. 16, 2008.
"Two dimensional real-time ultrasonic imaging of the heart and great vessels", Mayo Clin Proc. vol. 53:271-303, 1978.
An International Search Report dated Jun. 10, 2010, which issued during the prosecution of Applicant's PCT/IL09/01209.
An Office Action dated Apr. 6, 2010, which issued during the prosecution of Applicant's U.S. Appl. No. 12/484,512.
An International Search Report and a Written Opinion, both dated Aug. 17, 2010, which issued during the prosecution of Applicant's PCT/ILI0/00357.
Alfieri et al., "The edge to edge technique," The European Association for Cardio-Thoracic Surgery 14th Annual Meeting Oct. 7-11, Book of Proceed. (2000).
Alfieri et al., "An effective technique to correct anterior mitral leaflet prolapse," J Card Surg 14(6):468-470 (1999).
Alfieri et al., "The double orifice technique in mitral valve repair: a simple solution for complex problems," Journal of Thoracic Cardiovascular Surgery 122:674-681 (2001).
An International Search Report and a Written Opinion, both dated Feb. 10, 2011, which issued during the prosecution of Applicant's PCT/IL10/00890.
Alfieri, "The edge-to-edge repair of the mitral valve," [Abstract] 6th Annual NewEra Card. Care: Innovation & Technology, Heart Surg. Forum pp. 103. (2000).
Dang NC et al. "Simplified Placement of Multiple Artificial Mitral Valve Chords," The Heart Surgery Forum #2005-1005, 8 (3) (2005).
An Office Action dated Nov. 5, 2012, which issued during the prosecution of U.S. Appl. No. 12/795,026.
An Office Action dated Feb. 12, 2013, which issued during the prosecution of U.S. Appl. No. 12/926,673.
An International Search Report and a Written Opinion both dated Nov. 14, 2011, which issued during the prosecution of Applicant's PCT/IL11/00404.
An International Search Report and a Written Opinion both dated Nov. 23, 2011, which issued during the prosecution of Applicant's PCT/IL11/00446.
An International Preliminary Report on Patentability dated Nov. 27, 2012, which issued during the prosecution of Applicant's PCT/IL11/00404.
An Office Action dated Apr. 2, 2013, which issued during the prosecution of U.S. Appl. No. 12/785,717.
Office Action issued in U.S. Appl. No. 14/027,934 on Dec. 19, 2013.
Office Action issued in U.S. Appl. No. 12/785,717 on Dec. 27, 2013.
Office Action issued in U.S. Appl. No. 13/666,262 on Dec. 16, 2013.

* cited by examiner

FIG. 7
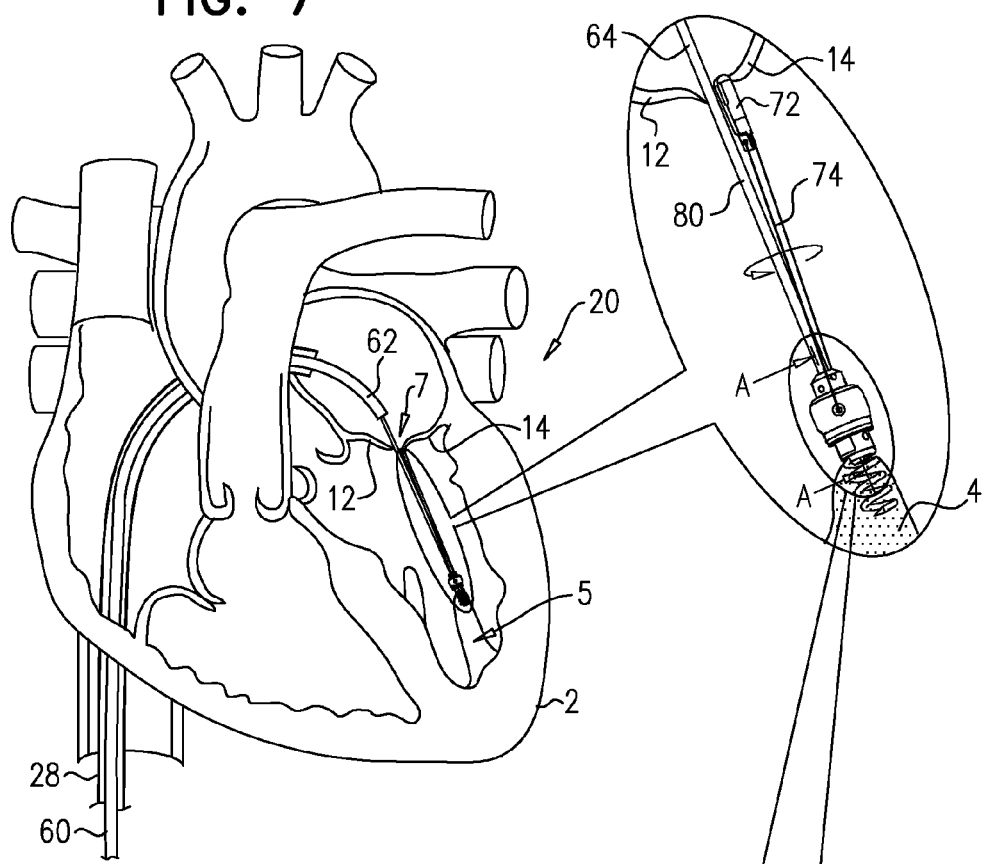
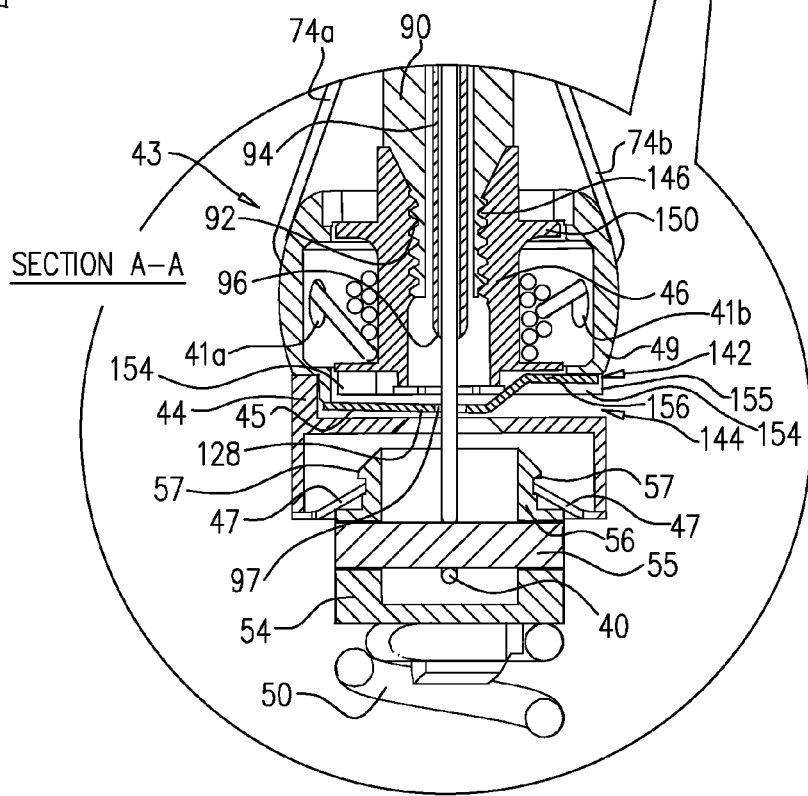
SECTION A-A

METHOD FOR GUIDE-WIRE BASED ADVANCEMENT OF A ROTATION ASSEMBLY

CROSS-REFERENCES TO RELATED APPLICATIONS

The present application is related to a U.S. regular application to Miller et al., entitled, "Apparatus for guide-wire based advancement of a rotation assembly," filed on even date herewith, which published as U.S. Patent Application Publication 2011/0106245 to Miller et al., and which is assigned to the assignee of the present patent application, and is incorporated herein by reference.

FIELD OF THE INVENTION

The present invention relates in general to valve and chordeae tendineae repair. More specifically, the present invention relates to repair of an atrioventricular valve and associated chordeae tendineae of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

U.S. Pat. No. 7,431,692 to Zollinger et al., which is incorporated herein by reference, describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

U.S. Patent Application Publication 2007/0118151 to Davidson, which is incorporated herein by reference, describes a method and system to achieve leaflet coaptation in a cardiac valve percutaneously by creation of neochordae to prolapsing valve segments. This technique is especially useful in cases of ruptured chordae, but may be utilized in any segment of prolapsing leaflet. The technique described herein has the additional advantage of being adjustable in the beating heart. This allows tailoring of leaflet coaptation height under various loading conditions using image-guidance, such as echocardiography. This offers an additional distinct advantage over conventional open-surgery placement of artificial chordae. In traditional open surgical valve repair, chord length must be estimated in the arrested heart and may or may not be correct once the patient is weaned from cardiopulmonary bypass. The technique described below also allows for placement of multiple artificial chordae, as dictated by the patient's pathophysiology.

U.S. Pat. No. 6,626,930 to Allen et al., which is incorporated herein by reference, describes apparatus and method for the stabilization and fastening of two pieces of tissue. A single device may be used to both stabilize and fasten the two pieces of tissue, or a separate stabilizing device may be used in conjunction with a fastening device. The stabilizing device may comprise a probe with vacuum ports and/or mechanical clamps disposed at the distal end to approximate the two pieces of tissue. After the pieces of tissue are stabilized, they are fastened together using sutures or clips. One exemplary application of a suture-based fastener comprises a toggle and suture arrangement deployed by a needle, wherein the needle enters the front side of the tissue and exits the blind side. In a second exemplary application, the suture-based fastener comprises a needle connected to a suture. The needle enters the blind side of the tissue and exits the front side. The suture is then tied in a knot to secure the pieces of tissue. One example of a clip-based fastener comprises a spring-loaded clip having two arms with tapered distal ends and barbs. The probe includes a deployment mechanism which causes the clip to pierce and lockingly secure the two pieces of tissue.

U.S. Pat. No. 6,629,534 to St. Goar et al., which is incorporated herein by reference, describes methods, devices, and systems are provided for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. Preferably, the tissue structures will be temporarily modified prior to permanent modification. For example, opposed valve leaflets may be temporarily grasped and held into position prior to permanent attachment.

U.S. Pat. No. 6,752,813 to Goldfarb et al., which is incorporated herein by reference, describes methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation.

U.S. Patent Application Publication 2003/0105519 to Fasol et al., which is incorporated herein by reference, describes artificial chordae having a strand member and a first and second pair of sutures at either longitudinal end of the strand member. The artificial chordae is preferably a unitary unit, formed from inelastic flexible material. In one application, the artificial chordae comprises multiple strand members joined together at a joined end. Different sized artificial chordae are provided sized to fit the patient's heart. The appropriately sized artificial chordae is chosen by using a chordae sizing gauge having a shaft and a transverse member, to measure the space within the patient's heart where the artificial chordae is attached.

The following patents and patent application publications may be of interest:
PCT Publication WO 06/097931 to Gross et al.
PCT Publication WO 07/136,783 to Cartledge et al.
PCT Publication WO 10/004,546 to Gross et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Patent Application Publication 2003/0050693 to Quijano et al
U.S. Patent Application Publication 2003/0167062 to Gambale et al.
U.S. Patent Application Publication 2004/0024451 to Johnson et al.
U.S. Patent Application Publication 2004/0148021 to Cartledge et al.
U.S. Patent Application Publication 2004/0236419 to Milo
U.S. Patent Application Publication 2005/0171601 to Cosgrove et al.
U.S. Patent Application Publication 2005/0216039 to Lederman
U.S. Patent Application Publication 2005/0288781 to Moaddeb et al.
U.S. Patent Application Publication 2007/0016287 to Cartledge et al.
U.S. Patent Application Publication 2007/0080188 to Spence et al.
U.S. Patent Application Publication 2008/0262609 to Gross et al.
U.S. Patent Application Publication 2009/0177266 to Powell et al.

SUMMARY OF THE INVENTION

In some applications of the present invention, apparatus is provided comprising one or more primary adjustable repair chords and an adjustment mechanism that is configured to adjust a tension of the one or more adjustable repair chords and that is slidable along a guide wire toward an implantation site. Additionally, the apparatus comprises a first tissue-engaging element (e.g., a tissue anchor) that comprises one or more docking stations. A respective guide wire is reversibly coupled to each one of the docking stations. The adjustment mechanism is slidable along the guide wire toward one of the one or more docking stations, and is coupled to the tissue-engaging element via the docking station. Thus, the docking station is a coupling element that provides coupling between two other elements (in this case, between adjustment mechanism and the tissue-engaging element.) The repair chord comprises a flexible, longitudinal member (e.g., sutures or wires). The repair chord is coupled at a distal portion thereof to the adjustment mechanism. In some applications, the repair chord functions as artificial chordae tendineae. In other applications, the repair chord is used to adjust a distance between two portions of the ventricular wall. For some applications, the repair chord is coupled at a proximal portion thereof to a second tissue-engaging element.

Typically, during a transcatheter procedure, the first tissue-engaging element is coupled to a first portion of tissue at a first implantation site in a heart of a patient. The adjustment mechanism is then slid along the guide wire and toward the first tissue-engaging element at the first implantation site. The proximal portion of the repair chord is then coupled via the second tissue-engaging element to a second portion of tissue at a second implantation site. Following the coupling of the second tissue-engaging element to the second implantation site, the adjustment mechanism is further slid distally toward the first tissue-engaging element and is then coupled to the first tissue-engaging element via the one or more docking stations on the first tissue-engaging element. Following the coupling of the adjustment mechanism to the second tissue-engaging element, a length and tension of the repair chord is then adjusted in order to adjust a distance between the first and second implantation sites. For applications in which the repair chord functions as an artificial chordea tendinea, the adjustment of the length and tension of the repair chord draws the leaflets together, and/or pulls the leaflet down toward the first implantation site.

In some applications of the present invention, the adjustment mechanism comprises a spool assembly which adjusts a degree of tension of the repair chord. The spool assembly comprises a housing, which houses a spool to which a distal portion of the repair chord is coupled.

For applications in which the repair chord is coupled to two respective portions of the ventricular wall, the two portions are drawn together, thereby restoring the dimensions of the heart wall to physiological dimensions, and drawing the leaflets toward one another.

In some applications of the present invention, the adjustment mechanism comprises a reversible locking mechanism which facilitates bidirectional rotation of the spool in order to effect both tensioning and relaxing of the repair chord. That is, the spool is wound in one direction in order to tighten the repair chord, and in an opposite direction in order to slacken the repair chord. Thus, the spool adjustment mechanism facilitates bidirectional adjustment of the repair chord.

In some applications of the present invention, the adjustable repair chord is implanted during an open-heart procedure. In these applications, the delivery tool comprises a handle and a multilumen shaft that is coupled at a distal end thereof to the adjustment mechanism. The delivery tool functions to advance the adjustment mechanism to the first portion of tissue, implant the adjustment mechanism at the first portion of tissue, and effect adjustment of the repair chord by effecting rotation of the spool. For applications in which the repair chord functions as an artificial chordea tendinea, prior to implantation of the adjustment mechanism, the distal portion of the delivery tool and the adjustment mechanism coupled thereto are advanced between the leaflets of the atrioventricular valve and into the ventricle toward the first portion of tissue. The incision made in the heart is then closed around the delivery tool and the heart resumes its normal function during the adjustment of the length of the artificial chordea tendinea.

In some applications of the present invention, apparatus and method described herein may be used for providing artificial chordae tendineae in a left ventricle of the heart and effecting adjustment thereof. In some applications, apparatus and method described herein may be used for providing artificial chordae tendineae in a right ventricle of the heart and effecting adjustment thereof. In some applications, apparatus and method described herein may be used for providing a system to adjust a length between two portions of the heart wall.

There is therefore provided, in accordance with some applications of the present invention, a method including:
coupling a tissue-engaging element to a first portion of cardiac tissue of a heart of a patient;
advancing toward the tissue-engaging element an adjustment mechanism along at least a portion of at least one guide member that is removably coupled to the tissue-engaging element, the adjustment mechanism engaging at least a first portion of at least a first flexible longitudinal member;

coupling a second portion of the first flexible longitudinal member to a second portion of cardiac tissue;

following the coupling of the second portion of the first flexible longitudinal member to the second portion of cardiac tissue:

sliding the adjustment mechanism further along the guide member; and coupling the adjustment mechanism to the tissue-engaging element; and using the adjustment mechanism, adjusting a length of the first flexible longitudinal member between the first and second portions of cardiac tissue.

In some applications of the present invention, coupling the tissue-engaging element to the first portion of cardiac tissue includes coupling the tissue-engaging element to a papillary muscle of a ventricle of the patient.

In some applications of the present invention, coupling the tissue-engaging element to the first portion of cardiac tissue includes coupling the tissue-engaging element to a portion of an inner wall of a ventricle of the patient.

In some applications of the present invention, adjusting the length of the flexible longitudinal member includes adjusting a distance between the first and second portions of cardiac tissue.

In some applications of the present invention, adjusting the length of the flexible longitudinal member includes adjusting the length of the flexible longitudinal member during beating of the heart of the patient.

In some applications of the present invention, adjusting the length of the flexible longitudinal member includes adjusting the length of the flexible longitudinal member during a first period thereof, and the method further includes further adjusting the length of the flexible longitudinal member during a second period that is after the first period.

In some applications of the present invention, coupling the tissue-engaging element to the first portion of cardiac tissue includes coupling the tissue-engaging element to an intracardiac portion of tissue in a manner in which a distal portion of the tissue-engaging element does not extend beyond an epicardium of the heart of the patient.

In some applications of the present invention, coupling the second portion of the flexible longitudinal member to the second portion of cardiac tissue includes coupling the second portion of the flexible longitudinal member to at least one leaflet of an atrioventricular valve of the patient.

In some applications of the present invention, coupling the second portion of the flexible longitudinal member to the second portion of cardiac tissue includes coupling the second portion of the flexible longitudinal member to exactly one leaflet of an atrioventricular valve of the patient.

In some applications of the present invention, coupling the second portion of the flexible longitudinal member to the second portion of cardiac tissue includes coupling, to a leaflet of an atrioventricular valve, a clip that is coupled to the second portion of the flexible longitudinal member.

In some applications of the present invention, coupling the adjustment mechanism to the tissue-engaging element includes locking the adjustment mechanism to a docking station coupled to the tissue-engaging element.

In some applications of the present invention, advancing the adjustment mechanism includes transcatheterally advancing the adjustment mechanism.

In some applications of the present invention, advancing the adjustment mechanism includes threading the guide member through an opening in the adjustment mechanism prior to the advancing.

In some applications of the present invention, the method further includes:

advancing a first portion of a second flexible longitudinal member, toward the tissue-engaging element; and coupling a second portion of the second flexible longitudinal member to a third portion of cardiac tissue.

In some applications of the present invention, the method further includes coupling the first portion of the second flexible longitudinal member to the tissue-engaging element following the coupling of the second portion of the second flexible longitudinal member to the third portion of cardiac tissue.

In some applications of the present invention:

the second portion of cardiac tissue includes a portion of tissue of a ventricle of the patient, coupling the second portion of the first flexible longitudinal member to the second portion of cardiac tissue includes coupling the second portion of the first flexible longitudinal member to the portion of tissue of the ventricle of the patient, the third portion of cardiac tissue includes at least one leaflet of an atrioventricular valve of the heart of the patient, and coupling the second portion of the second flexible longitudinal member to the third portion of cardiac tissue includes coupling the second portion of the second flexible longitudinal member to the at least one leaflet of the atrioventricular valve.

In some applications of the present invention, coupling the tissue-engaging element to the first portion of tissue includes coupling a tissue-engaging element coupled to at least first and second docking stations, the first and second docking stations being removably coupled to first and second guide members, respectively.

In some applications of the present invention:

advancing the adjustment mechanism includes:

advancing a first adjustment mechanism along the first guide member, the first adjustment mechanism engaging at least a first portion of at least a first flexible longitudinal member; and coupling the first adjustment mechanism to the first docking station, and the method further includes:

advancing a second adjustment mechanism along the second guide member, the second adjustment mechanism engaging at least a first portion of at least a second flexible longitudinal member; and coupling the second adjustment mechanism to the second docking station.

In some applications of the present invention, coupling the second portion of the flexible longitudinal member to the second portion of cardiac tissue includes coupling a second portion of the first flexible longitudinal member to the second portion of cardiac tissue, and the method further includes coupling a second portion of the second flexible longitudinal member to a third portion of cardiac tissue.

In some applications of the present invention:

the second portion of cardiac tissue includes a portion of tissue of a ventricle of the patient, coupling the second portion of the first flexible longitudinal member to the second portion of cardiac tissue includes coupling the second portion of the first flexible longitudinal member to the portion of tissue of the ventricle of the patient, the third portion of cardiac tissue includes at least one leaflet of an atrioventricular valve of the heart of the patient, and coupling the second portion of the second flexible longitudinal member to the third portion of cardiac tissue includes coupling the second portion of the second flexible longitudinal member to the at least one leaflet of the atrioventricular valve.

In some applications of the present invention, coupling the second portion of the flexible longitudinal member to the second portion of cardiac tissue includes coupling the second portion of the flexible longitudinal member to a portion of a wall of a ventricle of the patient, and adjusting the length of the flexible member includes adjusting a distance between the portion of the wall and the first portion of cardiac tissue.

In some applications of the present invention, adjusting the distance between the portion of the wall and the first portion of cardiac tissue includes adjusting a malpositioning of the heart wall of the patient.

In some applications of the present invention, the adjustment mechanism includes a spool coupled to the first portion of the flexible longitudinal member, and adjusting the length of the flexible longitudinal member using the adjustment mechanism includes rotating the spool.

In some applications of the present invention, the method further includes unwinding a portion of the at least one flexible longitudinal member from around the spool, and adjusting the length of the flexible longitudinal member includes applying tension to the flexible longitudinal member subsequently to the unwinding.

In some applications of the present invention, adjusting the length of the flexible longitudinal member includes:

applying tension to the flexible longitudinal member by winding successive portions of the flexible longitudinal member around the spool by rotating the spool in a first rotational direction thereof, and slackening the flexible longitudinal member by unwinding the successive portions of the flexible longitudinal member from around the spool by rotating the spool in a second rotational direction thereof opposite the first rotational direction.

In some applications of the present invention, the method further includes unlocking the spool prior to the adjusting the length of the flexible longitudinal member, and locking the spool following the adjusting the length of the flexible longitudinal member.

In some applications of the present invention:

the second portion of tissue includes at least one leaflet of an atrioventricular valve of the patient, the longitudinal member includes an artificial chordea tendinea, and coupling the adjustment mechanism to the tissue-engaging element includes:

advancing, between leaflets of the atrioventricular valve and into the ventricle, at least one shaft of a delivery tool, to which shaft the adjustment mechanism is removably coupled; and while the shaft remains coupled to the adjustment mechanism, coupling, using a coupling element holder of the delivery tool, at least one leaflet-engaging element to the at least one leaflet, the second portion of the artificial chordea tendinea is coupled to the at least one leaflet-engaging element.

In some applications of the present invention, advancing the at least one shaft includes transcatheterally advancing the at least one shaft.

In some applications of the present invention, coupling the at least one leaflet-engaging element to the at least one leaflet includes coupling the at least one leaflet-engaging element to exactly one leaflet.

In some applications of the present invention, using the coupling element holder of the delivery tool includes sliding the coupling element holder with respect to the guide member.

In some applications of the present invention:

the at least one flexible longitudinal member includes first and second cord portions thereof, each of the first and second cord portions having respective free ends, the first and second cord portions of the flexible longitudinal member extend from the adjustment mechanism, and coupling the second portion of the flexible longitudinal member to the second portion of cardiac tissue includes coupling each free end of the first and second cord portions to respective first and second leaflets of an atrioventricular valve of the patient.

In some applications of the present invention, adjusting the length of the flexible longitudinal member includes:

adjusting a length of the first cord portion of the longitudinal member between the adjustment mechanism and the first leaflet;

adjusting a length of the second cord portion of the longitudinal member between the adjustment mechanism and the second leaflet; and by the adjusting the lengths of the first and second portions of the longitudinal member, drawing together the first and second leaflets.

In some applications of the present invention, drawing together includes drawing together the first and second leaflets using a bead through which the first and second portions of the longitudinal member pass.

In some applications of the present invention, using the bead includes advancing the bead to ventricular surfaces of the first and second leaflets, and advancing the bead to the ventricular surfaces includes creating an edge-to-edge repair of the first and second leaflets.

There is additionally provided, in accordance with some applications of the present invention, apparatus, including:

a guide member;

a tissue-adjustment mechanism having:

an upper surface and a lower surface, at least one first opening at the upper surface, at least one second opening at the lower surface, and a channel extending between the first and second openings, the channel facilitating advancement of the tissue-adjustment mechanism along the guide member; and at least one repair chord coupled at a first portion thereof to the tissue-adjustment mechanism and having at least a first end that is configured to be coupled to a portion of tissue of a patient, the repair chord being configured to adjust a distance between the portion of tissue and the tissue-adjustment mechanism, in response to adjustment of the repair chord by the tissue-adjustment mechanism.

There is also provided, in accordance with some applications of the present invention, a method, including:

coupling a guide member to a portion of tissue of a patient; and advancing a tissue-adjustment mechanism toward the portion of tissue by:

threading a portion of the guide member through at least one channel extending between a first opening in an upper surface of the tissue-adjustment mechanism and a second opening in a lower surface of the tissue-adjustment mechanism; and advancing the tissue-adjustment mechanism along the guide member and toward the portion of tissue.

In some applications of the present invention, the method further includes removing entirely the guide member from the patient following the advancing the tissue-adjustment mechanism along the guide member.

In some applications of the present invention, the method further includes, prior to the coupling the guide member to the portion of tissue, reversibly coupling the guide member to a tissue anchor, and coupling the guide member to the portion of tissue of the patient includes implanting the tissue anchor in the portion of tissue of the patient.

The present invention will be more fully understood from the following detailed description of embodiments thereof, taken together with the drawings, in which:

BRIEF DESCRIPTION OF THE DRAWINGS

FIGS. 7-9 are schematic illustrations of adjusting by the adjustment mechanism a length of a repair chord coupled to the adjustment mechanism, in accordance with some applications of the present invention;

DETAILED DESCRIPTION OF EMBODIMENTS

Figure 1:
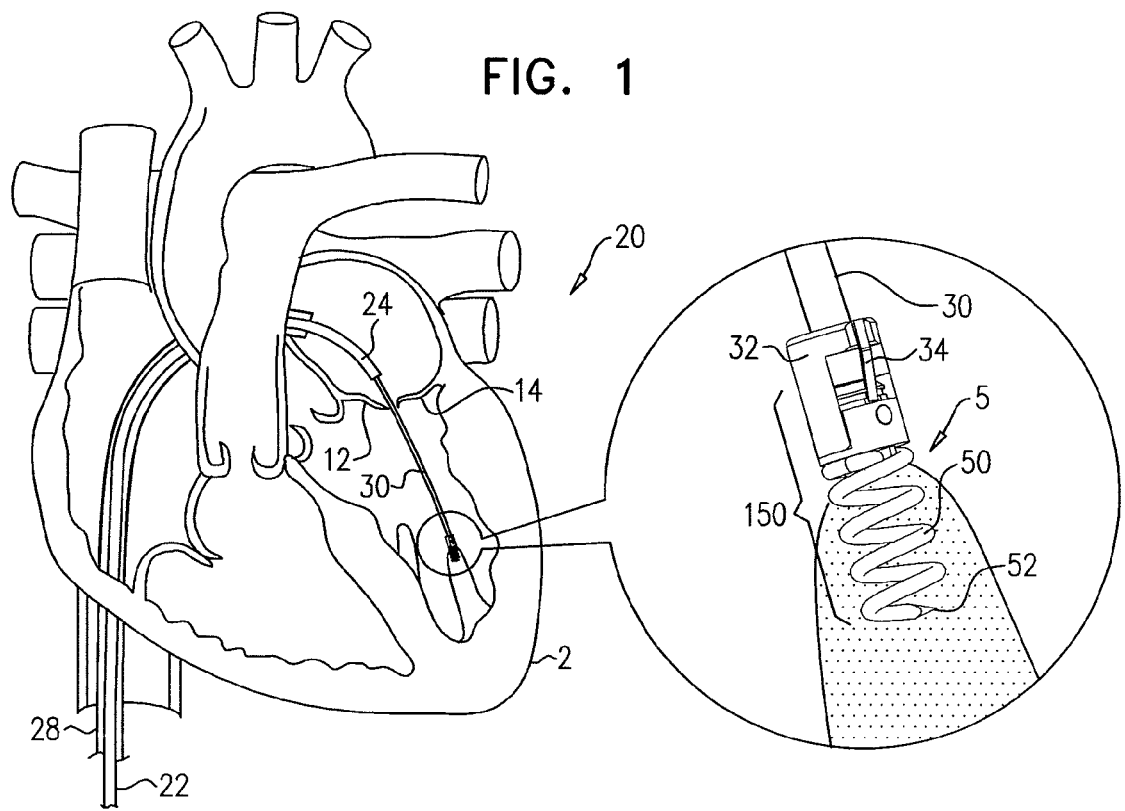
FIGS. 1-2 are schematic illustrations of apparatus comprising a tissue-engaging element comprising a docking station coupled to a guide wire, in accordance with some applications of the present invention.
Figure 2:
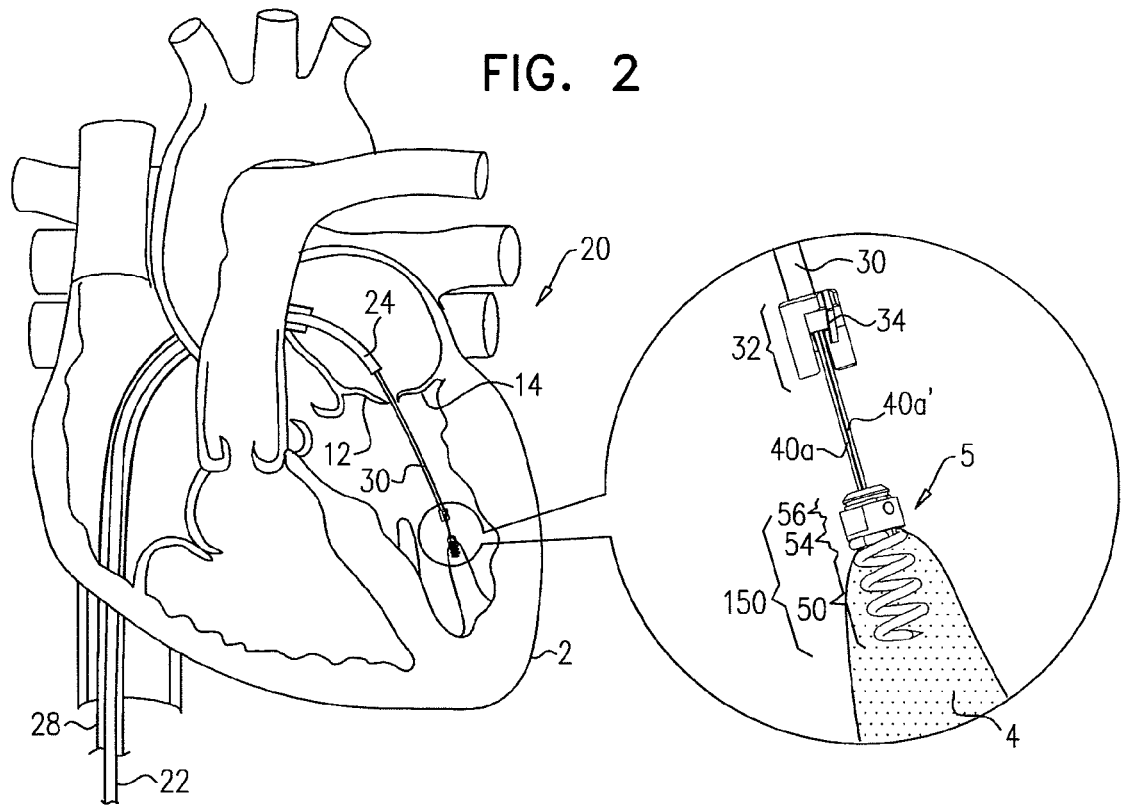

Reference is now made to FIGS. 1-2, which are schematic illustrations of a system 20 comprising a docking assembly 150 for implantation at a first implantation site 5 of a patient, in accordance with some applications of the present invention. Docking assembly 150 comprises a distal tissue anchor 50 (e.g., a helical tissue anchor as shown by way of illustration and not limitation), a docking platform 54, and at least one docking station 56, as shown in FIG. 2. At least one guide member, (e.g., a guide wire 40) is reversibly coupled to docking assembly 150 (e.g., by being looped around a portion of assembly 150) so as to define first and second portions 40a and 40a' that extend away from assembly 150.

Tissue anchor 50 is implanted within cardiac tissue in a manner in which a distal portion of anchor 50 does not extend beyond an epicardium of heart 2 of the patient. Thus, anchor 50 is implanted at an intracardiac site such that the adjustment mechanism that is eventually coupled thereto (as described hereinbelow) is implanted at the intracardiac site such that no portions of the adjustment mechanism extend beyond the epicardium of the heart.

Docking assembly 150 and guide wire 40 are advanced toward implantation site typically during a transcatheter procedure, as shown. However, it is to be noted that the scope of the present invention includes the advancement of assembly 150 and guide wire 40 during a minimally-invasive or open-heart procedure. The procedure is typically performed with the aid of imaging, such as fluoroscopy, transesophageal echo, and/or echocardiography.

The procedure typically begins with the advancing of a semi-rigid guide wire into a right atrium of the patient. The semi-rigid guide wire provides a guide for the subsequent advancement of a sheath 28 therealong and into the right atrium. Once sheath 28 has entered the right atrium, the semi-rigid guide wire is retracted from the patient's body. Sheath 28 typically comprises a 13-20 F sheath, although the size may be selected as appropriate for a given patient. Sheath 28 is advanced through vasculature into the right atrium using a suitable point of origin typically determined for a given patient. For example:

sheath 28 may be introduced into the femoral vein of the patient, through an inferior vena cava, into the right atrium, and into the left atrium transseptally, typically through the fossa ovalis;

sheath 28 may be introduced into the basilic vein, through the subclavian vein to the superior vena cava, into the right atrium, and into the left atrium transseptally, typically through the fossa ovalis; or sheath 28 may be introduced into the external jugular vein, through the subclavian vein to the superior vena cava, into the right atrium, and into the left atrium transseptally, typically through the fossa ovalis.

In some applications of the present invention, sheath 28 is advanced through the inferior vena cava of the patient (as shown) and into the right atrium using a suitable point of origin typically determined for a given patient.

Sheath 28 is advanced distally until the sheath reaches the interatrial septum. For some applications, a resilient needle and a dilator (not shown) are advanced through sheath 28 and into the heart. In order to advance sheath 28 transseptally into the left atrium, the dilator is advanced to the septum, and the needle is pushed from within the dilator and is allowed to puncture the septum to create an opening that facilitates passage of the dilator and subsequently sheath 28 therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 28 through the septum and into the left atrium is followed by the extraction of the dilator and the needle from within sheath 28. Subsequently, a docking-assembly delivery tool 30 is advanced through sheath 28. Tool 30 is typically advanced within a lumen of an advancement sheath 22 having a distal end 24. Advancement sheath 22 is advanced within sheath 28. Delivery tool 30 is coupled at a distal end thereof to a manipulator 32 which is reversibly coupled to docking station 56 and docking platform 54 of docking assembly 150. Manipulator 32 has lateral arms which cup platform 54, and manipulator has a docking-station-coupler 34, as shown in FIG. 1. Coupler 34 is biased to move radially-inward, as shown in FIG. 1. Docking station 56 is ribbed, such that coupler 34, when moved radially inward, engages at least one rib of docking station 56, thereby coupling assembly 150 to delivery tool 30.

Docking assembly 150 is implanted in implantation site 5 when tool 30 is rotated to rotate anchor 50 and corkscrew anchor 50 into tissue of site 5. Site 5 typically comprises a portion of tissue at an intraventricular site in heart 2 of the patient. As shown, site 5 includes a papillary muscle 4, by way of illustration and not limitation. It is to be noted that site 5 includes any portion of cardiac tissue, e.g., a portion of a free wall of the ventricle, a portion of the septum facing the ventricle, a portion of tissue at a base of the papillary muscle, or a portion of the wall at the apex of the ventricle. (For the purposes of the claims, "a portion of tissue of a ventricle" includes any portion of cardiac tissue, e.g., a portion of a free wall of the ventricle, a portion of the septum facing the ventricle, a portion of tissue at a base of the papillary muscle, or a portion of the wall at the apex of the ventricle.)

Following the implantation of assembly 150 at site 5, tool 30 is disengaged from assembly 150 when the physician pulls on tool 30. This pulling pulls on manipulator 32 such that coupler 34 is actively moved radially outward against the ribs of docking station 56, and is thereby decoupled from station 56. At the time of pulling, tissue at implantation site 5 pulls on assembly 150 so as to help disengage tool 30 from assembly 150.

As shown in FIG. 2, following the decoupling of tool 30 from assembly 150, tool 30 is pulled proximally along guide wire 40 and is extracted from the body of the patient together with advancement sheath 22, leaving behind assembly 150 and guide wire 40.

Figure 3:
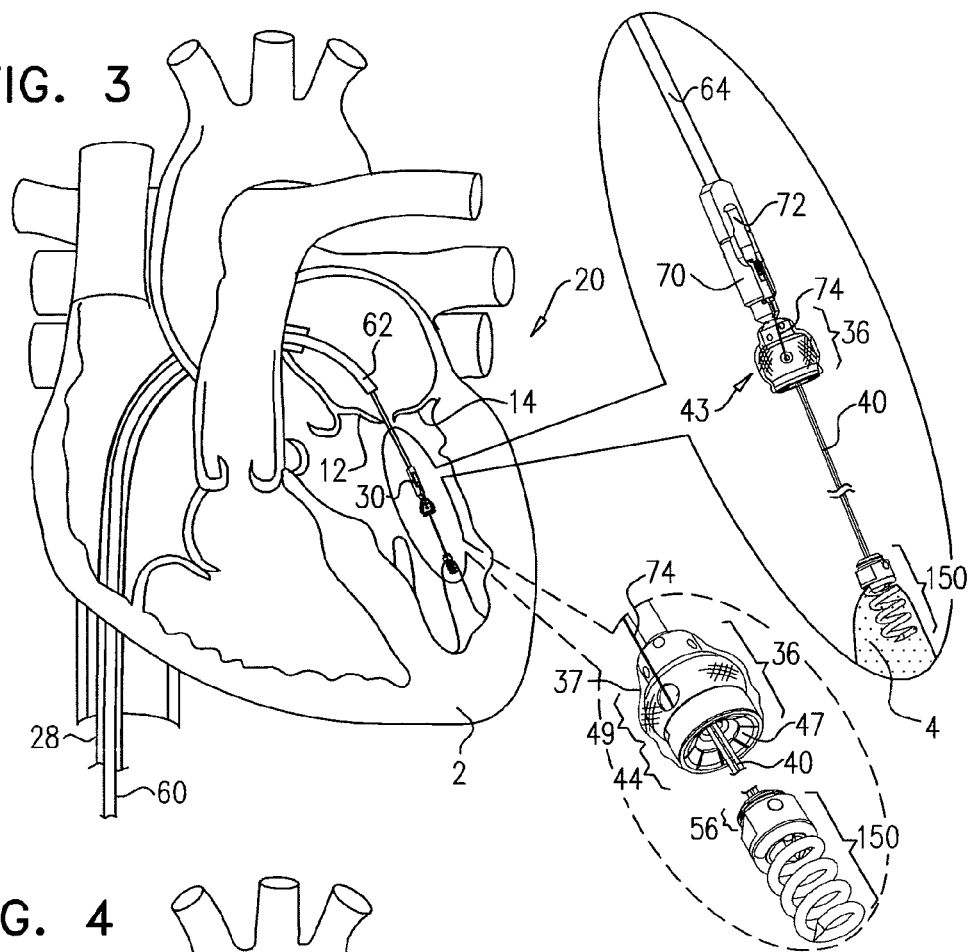
FIG. 3 is a schematic illustration of advancement of an adjustment mechanism along the guide wire toward the docking station of FIGS. 1 and 2, in accordance with some applications of the present invention.

FIG. 3 shows advancement of a spool assembly 36 comprising an adjustment mechanism 43, along guide wire 40 by an adjustment-mechanism delivery tool 64, in accordance with some applications of the present invention. Tool 64 is surrounded by and slidable within an advancement sheath 60 having a distal end 62. Spool assembly 36 is surrounded by a braided fabric mesh, e.g., a polyester mesh, which promotes fibrosis around assembly 36 and facilitates coupling of assembly 36 to tissue of heart 2. Assembly 36 houses a rotatable structure (e.g., a spool as shown hereinbelow) that is surrounded by a housing 49. Housing 49 is coupled to a distal cap 44 which facilitates coupling of assembly 36 to docking station 56 of docking assembly 150. As shown, cap 44 is shaped so as to define a plurality of baffles 47 that are disposed angularly with respect to a distal end of cap 44, and are coupled to the distal end of cap 44 along a coupling joint which facilitates slight movement of each baffle 47. During the coupling of spool assembly 36 to docking station 56, the ribbed portion of docking station 56 pushes inwardly baffles 47 of cap 44, as is described hereinbelow. Baffles 47 then expand and engage an area of docking station 56 between the ribs of the ribbed portion so as to dock and lock assembly 36 to docking station 56.

Additionally, cap 44 is shaped so as to define a central opening therethrough which facilitates passage through the opening of guide wire 40. Additionally, spool assembly 36 and the components thereof are shaped so as to define a central opening (i.e., an opening having the same axis as guide wire 40). That is, spool 46 has a central opening, and housing 49 has a central opening which facilitates passage of spool 46 and housing 49 along guide wire 40.

As shown, adjustment mechanism 43 is coupled to a distal portion of a repair chord 74 (e.g., repair chord 74 is looped through a portion of adjustment mechanism 43). For some applications, and as is described hereinbelow, chord 74 functions as an artificial chordea tendinea. A proximal portion of chord 74 is coupled to a leaflet-engaging element 72 (e.g., a clip, as shown). Leaflet-engaging element 72 is disposed within a holder 70 that is coupled to delivery tool 64. Chord 74 a superelastic, biocompatible material (e.g., nitinol, ePTFE, PTFE, polyester, stainless steel, or cobalt chrome). Typically, chord 74 comprises an artificial chordea tendinea.

Figure 4:
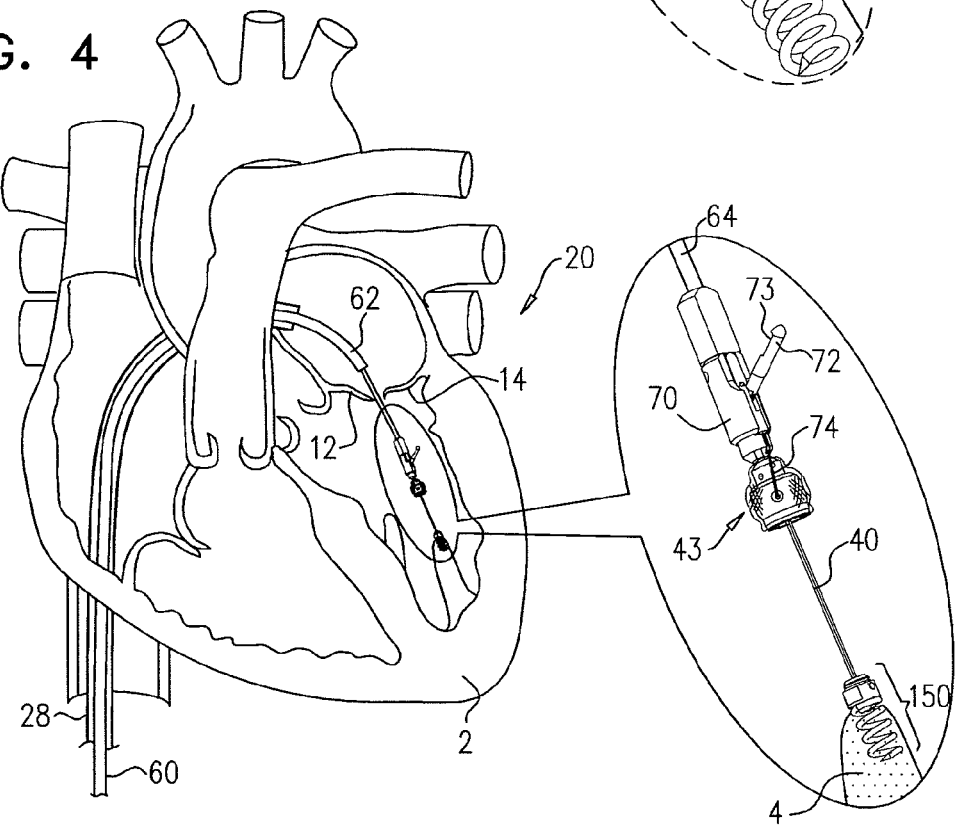
FIGS. 4-5 are schematic illustrations of engaging a leaflet with a leaflet engaging element, in accordance with some applications of the present invention.
Figure 5:
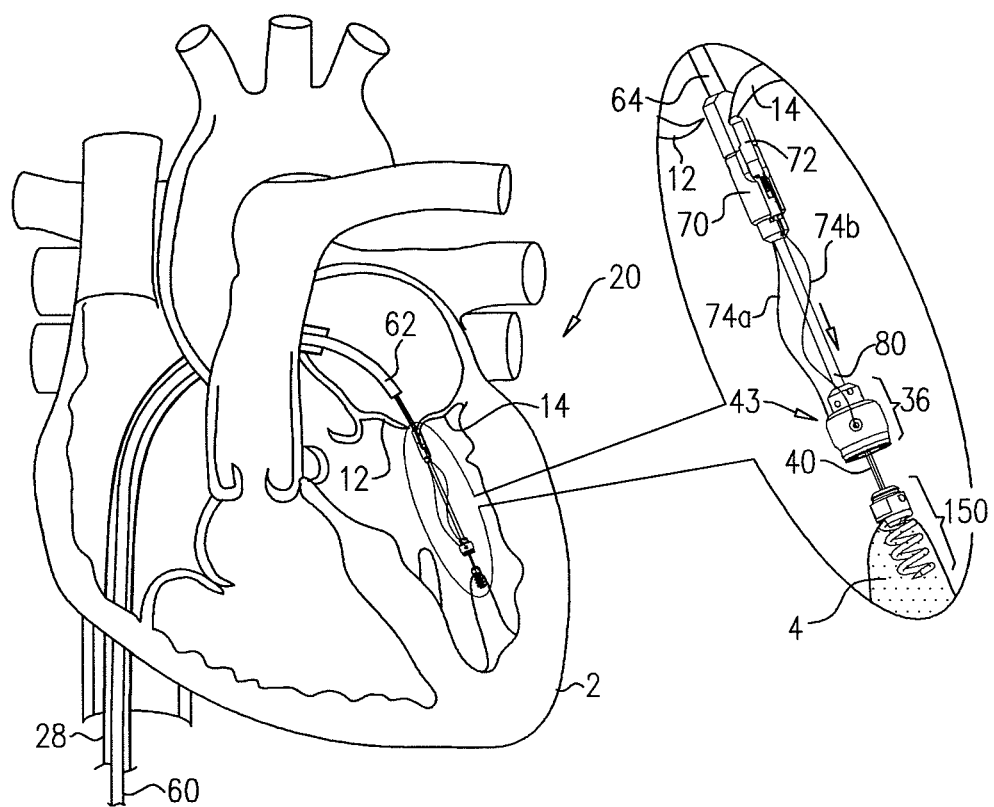

FIGS. 4-5 are schematic illustrations of the engaging of leaflet-engaging element 72 to at least one leaflet 14 of a mitral valve of the patient, in accordance with some applications of the present invention. As shown in FIG. 4, the clip is opened from a remote location outside the body of the patient.

For some applications, the clip typically is shaped so as to define at least one coupling protrusion 73. The clip has a tendency to close, and is initially held open by a cord (not shown) that is coupled to a surface of the clip, extends through delivery tool 64, and is held taught outside of the heart. Once the clip has been advanced to the desired location on the leaflet, the cord is relaxed, allowing the clip to close. The cord is removed, typically by releasing one end thereof and pulling the other end. The positioning of holder 70 between the leaflets (FIG. 5) helps ensure that the clip engages exactly one of the leaflets. It is noted that in FIG. 5 the clip is shown engaging only a single leaflet (leaflet 14). The clip typically engages the leaflet by clamping the leaflet such that the clip engages atrial and ventricular surfaces of the leaflet. The clip may puncture the leaflet, or may merely press firmly against the leaflet.

Holder 70 is shaped to define a groove which houses the clip during the advancement of tool 64 toward the ventricle. The groove functions as a track to facilitate slidable detachment of the clip from holder 70 following the engaging of the clip to leaflet 14.

Alternatively, the clip has a tendency to open. In order to close the clip, a cord is provided. A distal-most portion of the cord is looped around the clip. Once the clip has been advanced to the desired location on the leaflet, as shown in FIG. 5, the surgeon pulls on both ends of the cord, thereby causing the clip to become locked closed. The cord is removed, typically by releasing one end thereof and pulling the other end.

It is to be noted that the scope of the present invention includes any leaflet-engaging element known in the art. In particular techniques for use of leaflet-engaging element 72 may be practiced in combination with any one of the leaflet-engaging elements as described in U.S. patent application Ser. No. 12/548,991 to Maisano et al., entitled, "Implantation of repair chords in the heart," filed on Aug. 27, 2009, which published as U.S. Patent Application Publication 2010/0161042, and which is incorporated herein by reference.

As shown in FIG. 5, portions 74a and 74b extend from leaflet engaging element 72 toward adjustment mechanism 43. Portions 74a and 74b define portions of a single chord 74 that is looped through a portion of mechanism 43. Alternatively, portions 74a and 74b represent two distinct chords which are coupled at their distal ends to adjustment mechanism 43 and at their proximal ends to leaflet-engaging element 72.

As shown, leaflet-engaging element 72 engages leaflet 14 prior to coupling spool assembly 36 to docking station 56.

Figure 6:
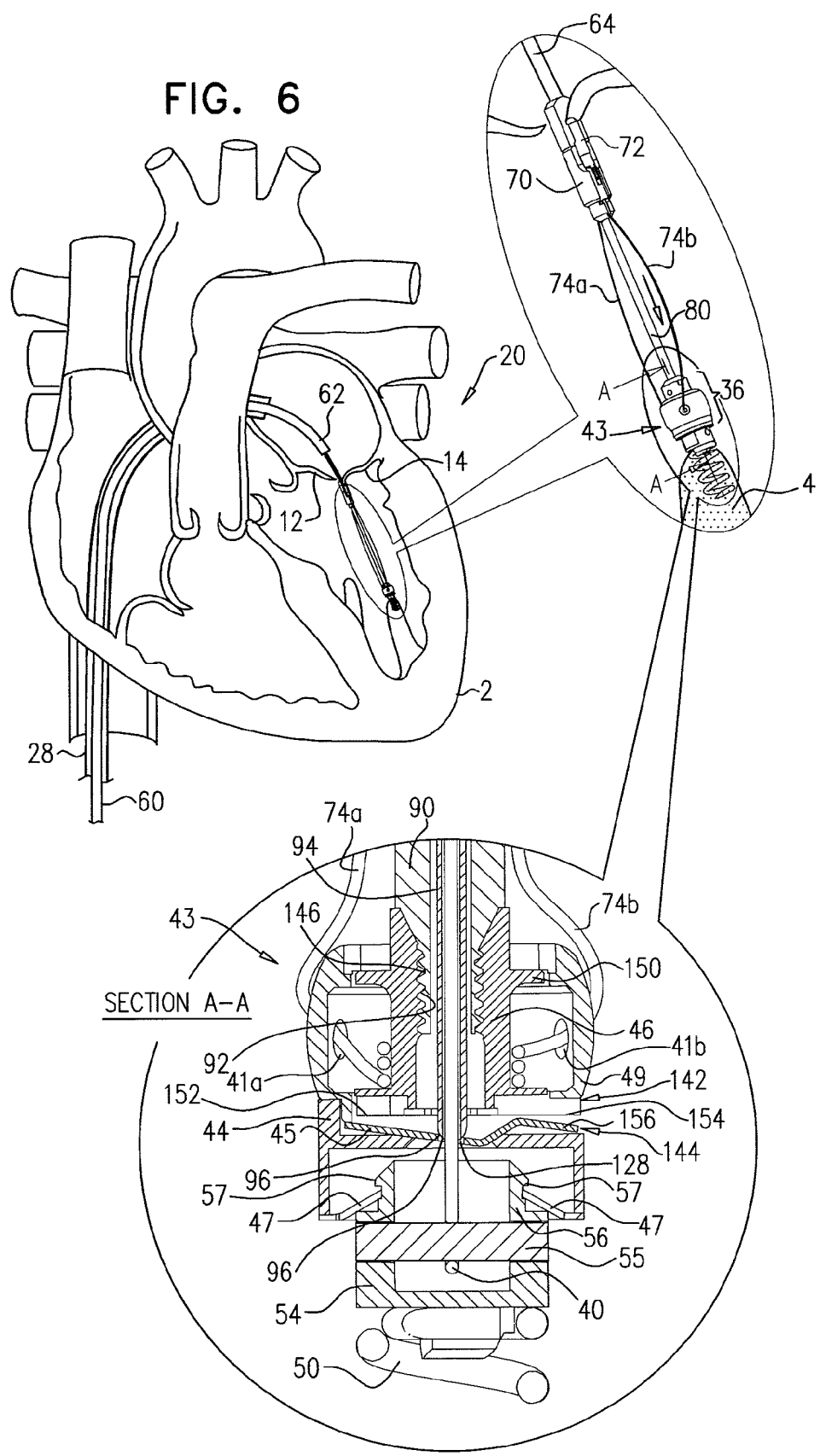
FIG. 6 is a schematic illustration of coupling of the adjustment mechanism of FIG. 3 to the docking station, in accordance with some applications of the present invention.

FIG. 6 shows spool assembly 36 being coupled to docking station 56, in accordance with some applications of the present invention. Following the coupling of leaflet-engaging element 72 to leaflet 14, spool assembly 36 is pushed distally toward docking station 56. Spool assembly 36 is coupled to an advancement shaft 80 which slides within a lumen of delivery tool 64 and within a lumen of holder 70 so as to advance spool assembly 36 while leaflet-engaging element 72 remains engaged with leaflet 14. Advancement shaft 80 functions to advance distally spool assembly 36 to facilitate engagement between spool assembly 36 and docking station 56. As described hereinabove, docking station 56 has one or more ribs 57 (shown in the enlarged cross-sectional image of FIG. 6) which project laterally such that rib 57 defines a shelf and an area underneath the shelf that is depressed. As described hereinabove, cap 44 of assembly 36 is shaped so as to define a plurality of baffles 47. As cap 44 engages docking station 56, baffles 47 are pushed inward and upward angularly as each baffle slides against rib 57. After each baffle 47 passes the shelf of rib 57, the baffle engages the depressed portion underneath rib 57, as shown in the enlarged cross-sectional image of FIG. 6. The shelf of rib 57 prevents upward movement of baffles 47 and thereby locks in place baffles 47 and cap 44 with respect to docking station 56. Rib 57 therefore comprises a locking mechanism to lock adjustment mechanism 43 to tissue anchor 50.

Following the coupling of assembly 36 to docking station 56, spool 46 is rotated in a first direction thereof in order to advance with respect to spool 46 (e.g., loop around spool 46) and contact with spool 46 successive portions chord 74. The rotating of spool 46 in the first direction thereof pulls tight and adjusts a length of chord 74 between leaflet 14 and spool 46, in order to adjust a distance between leaflet 14 and implantation site 5, as is described hereinbelow. Housing 49 is shaped so as to provide openings 41a and 41b for passage therethrough of portions 74a and 74b, respectively, of chord 74 into housing 49. For some applications of the present invention, portions 74a and 74b define portions of a single chord 74 that is looped through spool 46. For other applications, portions 74a and 74b define discrete chords which are each coupled at respective distal ends thereof to spool 46.

The enlarged, cross-sectional image of FIG. 6 shows spool 46 within housing 49. Spool 46 defines an upper surface 150, a lower surface 152, and a cylindrical body portion disposed vertically between surfaces 150 and 152. Spool 46 is shaped to provide a driving interface, e.g., a channel, which extends from an opening provided by upper surface 150 to an opening provided by lower surface 152. A proximal portion of the driving interface is shaped to define a threaded portion 146 which may or may not be tapered. Threaded portion 146 of spool 46 is engageable by a threaded portion of a screwdriver head 92 of a screwdriver 90. Rotation of screwdriver head 92 rotates spool 46 as the respective threaded portions of spool 46 and screwdriver head 92 engage. The cylindrical body portion of spool 46 is shaped to define one or more holes which function as respective coupling sites for coupling (e.g., looping through the one or more holes, or welding to spool 46 in the vicinity of the one or more holes) of any number of chords 74 to spool 46.

Lower surface 152 of spool 46 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially or otherwise with respect to lower surface 152 of spool 46.

As shown, a locking mechanism 45 is disposed in communication with lower surface 152 of spool 46 and disposed in communication with at least in part to a lower surface of housing 49. Typically, a cap 44 maintains locking mechanism 45 in place with respect to lower surface 152 of spool 46 and lower surface of housing 49. For some applications, locking mechanism 45 is coupled, e.g., welded, to the lower surface of housing 49. Typically, locking mechanism 45 defines a mechanical element having a planar surface that defines slits. It is to be noted that the surface of locking mechanism 45 may also be curved, and not planar. Locking mechanism 45 is shaped to provide a protrusion 156 which projects out of a plane defined by the planar surface of the mechanical element. The slits of mechanism 45 define a depressible portion 128 that is disposed in communication with and extends toward protrusion 156. Depressible portion 128 is moveable in response to a force applied thereto typically by an elongate locking mechanism release rod 94 which slides through a lumen of screwdriver 90 and a torque-delivering tool that is coupled thereto. Techniques for using screwdriver 90 and locking mechanism 45 may be practiced in combination with any one of the apparatus and techniques as described in U.S. Provisional Patent Application 61/265,936 to Miller et al., entitled, "Delivery tool for implantation of spool assembly coupled to a helical anchor," filed Dec. 2, 2009, which is incorporated herein by reference.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

Cap 44 is provided that is shaped to define a planar surface and an annular wall having an upper surface thereof. The upper surface of the annular wall is coupled to, e.g., welded to, a lower surface provided by housing 49. The annular wall of cap 44 is shaped to define a recessed portion 144 of cap 44 that is in alignment with a recessed portion 142 of spool housing 49.

As shown, a distal end 96 of locking mechanism release rod 94 pushes distally on depressible portion 128 in order to unlock locking mechanism 45 from spool 46. Pushing depressible portion 128 by locking mechanism release rod 94 pushes distally protrusion 156 within recessed portion 142 of housing 49 and within recessed portion 144 of cap 44, which frees protrusion 156 from recesses 154 of spool 46. Once protrusion 156 is released from recesses 154 of spool 46, the physician is able to rotate spool 46 bidirectionally in order to adjust a tension of chord 74.

When the physician rotates spool 46 in the first rotational direction, chord 74 is pulled tight, and leaflet 14 is drawn toward adjustment mechanism 40 and toward anterior leaflet 12 of mitral valve 8.

In the resting state (i.e., prior to the rotation of spool 46 in order to adjust chord 74, following coupling of leaflet-engaging element 72 to leaflet 14) chord 74 is wrapped around spool 46 a few times (e.g., three times, by way of illustration and not limitation). This winding provides excess slack to chord 74 (in case portions 74a and 74b are coupled too tightly to leaflet 14). If the physician wishes to provide slack to member 74 or to any one of portion 74a or 74b, the physician unwinds a bit of the wrapped portion of member 74 from around spool 46 (e.g., by unwinding chord 74 a few times from around spool 46, or by unwinding chord 74 entirely from around spool 46 so that chord 74 slides freely through spool 46 within a channel provided therein). In order to accomplish such unwinding, the physician rotates spool 46 in a rotational direction in which it unwinds the wrapped portion of chord 74. Since chord 74 is looped through spool 46 in the channel provided therein, when chord 74 is unwound from spool 46, the physician can pull on one or both portions 74a and 74b so as to adjust, make even, or further slacken any one of or both portions 74a and 74b that extend from spool 46.

When the physician desires to pull tight chord 74, he or she effects rotation of spool 46 in a first rotational direction, i.e., the direction opposite the second rotational direction in which spool 46 is rotated during the unwinding of chord 74 from spool 46. Rotation of spool 46 in the first rotational direction winds chord 74 around spool 46, while rotation of spool 46 in a second rotational direction opposite the first rotational direction, unwinds the portion of longitudinal chord 74 from around spool 46.

FIG. 7 shows spool assembly 36 following the adjustment of chord 74 by rotating screwdriver 90 in the direction as indicated by the arrow, and the partial removal of screwdriver 90, in accordance with some applications of the present invention. As shown in the enlarged cross-sectional image of FIG. 7, successive portions of chord 74 are wrapped around spool 46. That is, chord 74 is wrapped more times around spool 46 following adjustment (e.g., an additional 4 times, as shown in FIG. 7), than prior to adjustment (FIG. 6). This pulls chord 74 from a slackened state (FIG. 6) to a taut state (FIG. 7) in order to adjust a length of chord 74 between adjustment mechanism 43 and the proximal end of chord 74 that is coupled to leaflet-engaging element 72. Additionally, this applying of tension to chord 74 adjusts a length between first and second implantation sites 5 and 7. Typically, chord 74 is adjusted while heart 2 is beating.

As shown, rod 94 is shaped so as to define a central lumen and a distal opening for passage therethrough of guide wire 40. Additionally, depressible portion 128 is shaped so as to provide an opening for passage of guide wire 40 therethrough. Guide wire 40 is looped around a distal looping element 55 of docking platform 54 of docking assembly 150. Following the adjusting of the tension and length of chord 74, screwdriver 90 is decoupled from spool 46 (e.g., by being unscrewed from threaded portion 146 of spool 46) and is advanced proximally together with rod 94 away from spool assembly 36, as shown in the enlarged, cross-sectional image of FIG. 7. Guide wire 40 remains coupled to docking platform 54 and docking assembly 150 following removal of screwdriver 90. Guide wire 40 then facilitates subsequent advancement of screwdriver 90 or any other tool to access spool assembly 36 and/or to facilitate further adjustment of chord 74 beyond the initial adjustment. Guide wire 40 may remain chronically coupled to docking assembly 150 and accessible at a subcutaneous location of the patient, e.g., a port. For other applications, guide wire 40 is removed from docking assembly 150 when the physician determines that further adjustment of chord 74 is not needed. The physician removes guide wire 40 by pulling from outside the body of the patient, one end of guide wire 40 so that guide wire 40 slides around element 55 and is unlooped therefrom. The physician continues to pull on the end of guide wire 40 until the second end is exposed and removed from the patient.

Following the removal of locking-mechanism release rod 94, depressible portion 128 is no longer depressed by distal end 96 of rod 94, and protrusion 156 returns within a recess 154 of spool 46 so as to lock spool 46 in place and restriction rotation thereof in either direction.

Reference is now made to FIGS. 3-7. It is to be noted that spool assembly 36 is only coupled to docking assembly 150 following the coupling of leaflet-engaging element 72 to leaflet 14. This is done in order to reduce the strain on implantation site 5. Should spool assembly 36 be implanted at implantation site 5 prior to engaging leaflet 14 with leaflet-engaging element 72, more strain would be applied to implantation site 5 than if spool assembly 36 been implanted following the coupling of leaflet-engaging element 72 to leaflet 14, as described herein.

Figure 8:
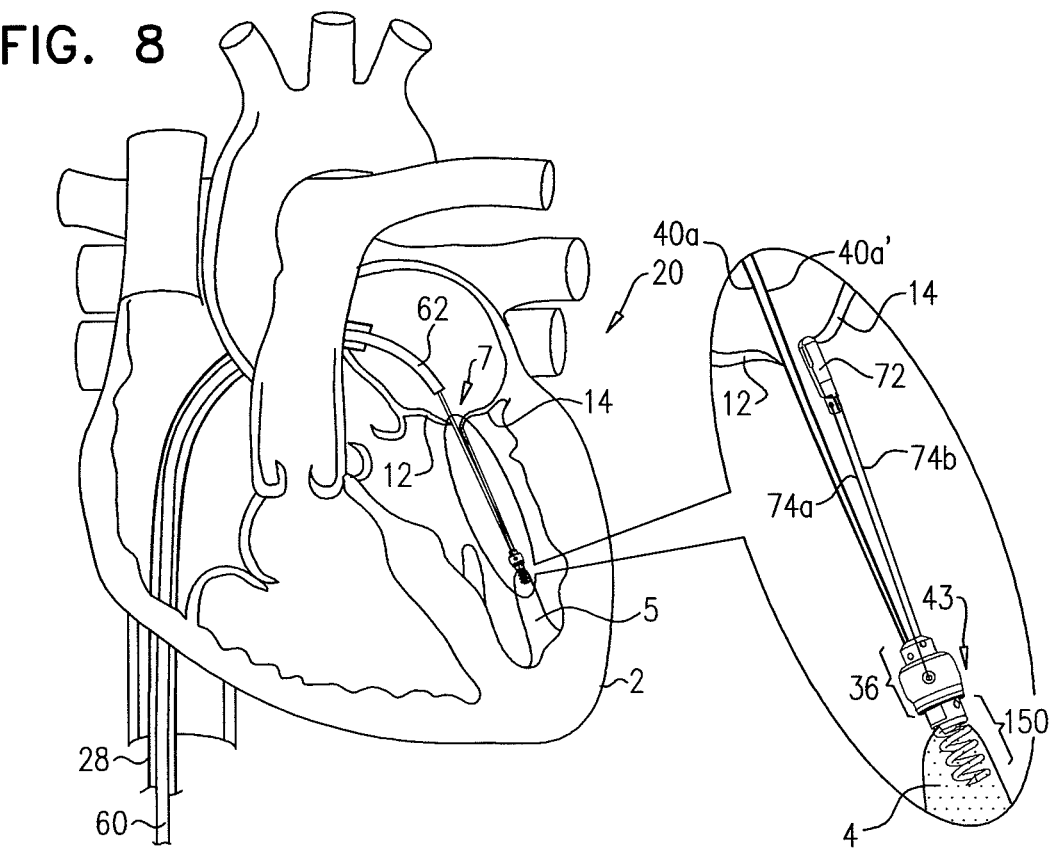

FIG. 8 shows system 20 following removal of the tool used to rotate spool 46 of spool assembly 36, in accordance with some applications of the present invention. As shown, chord 74 is pulled tight such that its length and tension are adjusted, and leaflet 14 is pulled and adjusted commensurate with the adjustment of chord 74. Guide wire 40 remains coupled to spool assembly 36 and to docking assembly 150, as shown, such that portions 40a and 40a' extend from spool assembly 36. Guide wire 40 facilitates the reintroduction of the tool used to rotate spool 46, or of any other tool.

Figure 9:
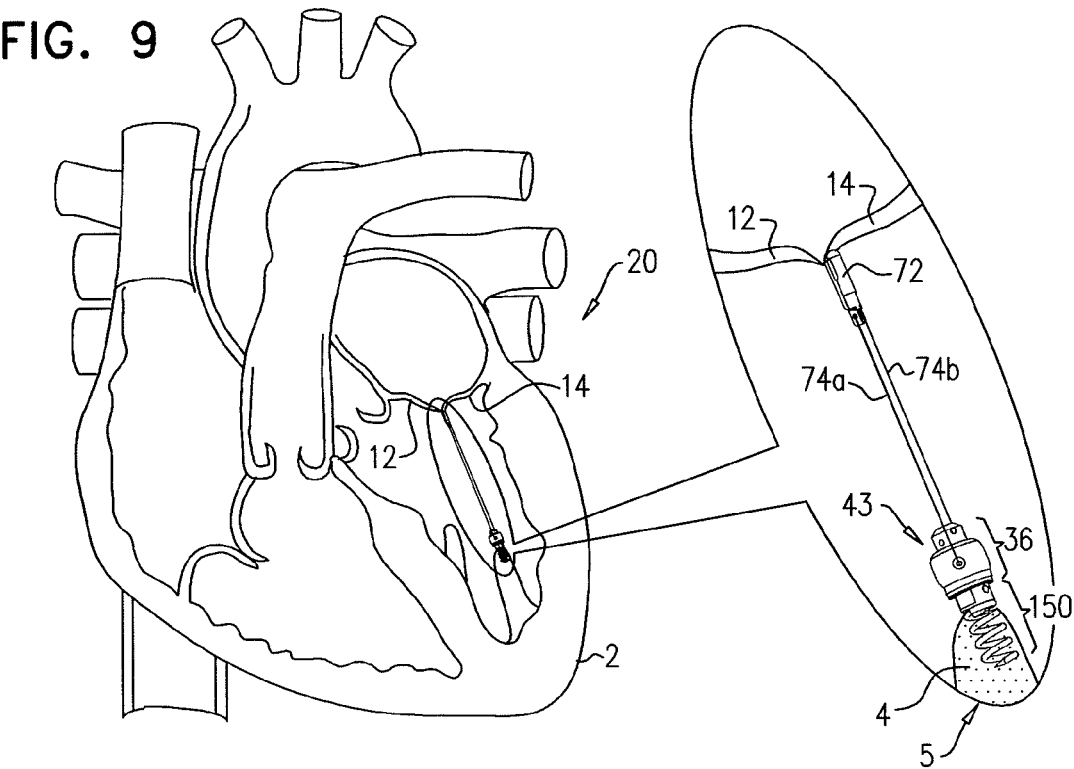

FIG. 9 shows system 20 following the removal of guide wire 40 from heart 2, in accordance with some applications of the present invention. As shown, the adjustment of chord 74 draws leaflets 12 and 14 together.

Figure 10:
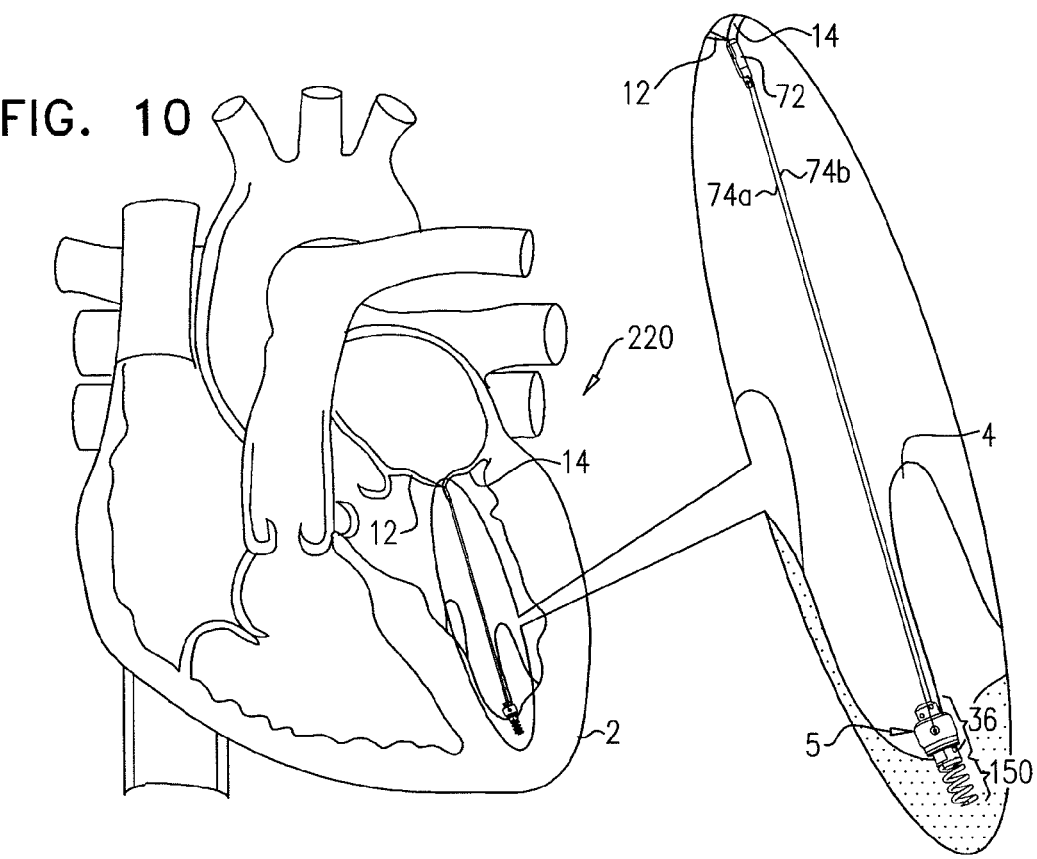
FIG. 10 is a schematic illustration of the adjustment mechanism and the repair chord, in accordance with some other applications of the present invention.

FIG. 10 shows a system 220, as described hereinabove, with the exception that implantation site 5 includes tissue of the wall of the ventricle at the base of papillary muscle 4 in a vicinity of the apex of the heart, in accordance with some applications of the present invention. Implantation site 5 is shown by way of illustration and not limitation, and as described hereinabove, site 5 may include any portion of tissue of heart 2.

FIGS. 11-15 are schematic illustrations of a system 320 comprising a multiple-docking-station assembly 350 comprising a plurality of docking stations 56, in accordance with some applications of the present invention. Multiple-docking-station assembly 350 comprises a tissue anchor 50 and a docking platform 322 which supports two or more docking stations 56. Platform 322 supports three docking stations 56a, 56b, and 56c, by way of illustration and not limitation. Platform 322 may support any number of docking stations 56. As shown, each docking station 56a, 56b, and 56c is reversibly coupled to a respective guide wire 40a, 40b, and 40c, in a manner as described hereinabove. Each docking station 56a, 56b, and 56c facilitates coupling thereto of a respective spool assembly 36a, 36b, and 36c, or any other tool or device which may be coupled to docking stations 56a, 56b, and 56c.

Figure 11:
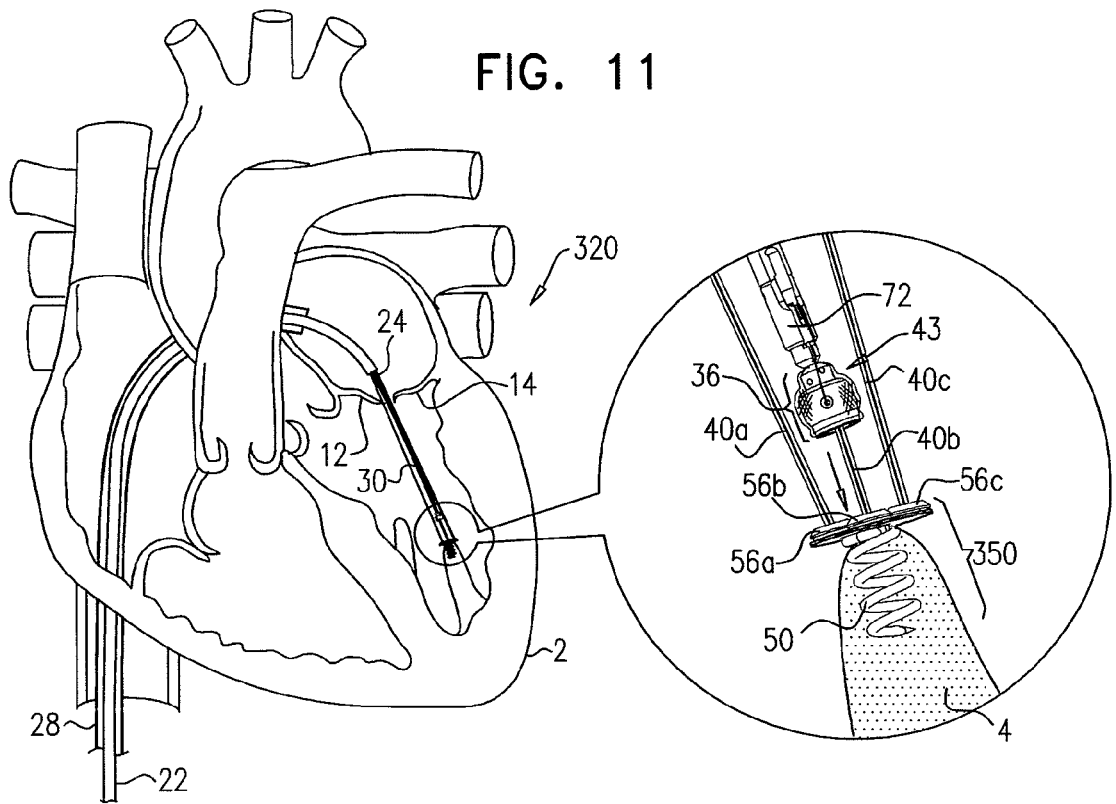
FIGS. 11-15 are schematic illustrations of a plurality of docking stations and a plurality of adjustment mechanisms, in accordance with some applications of the present invention.
Figure 12:
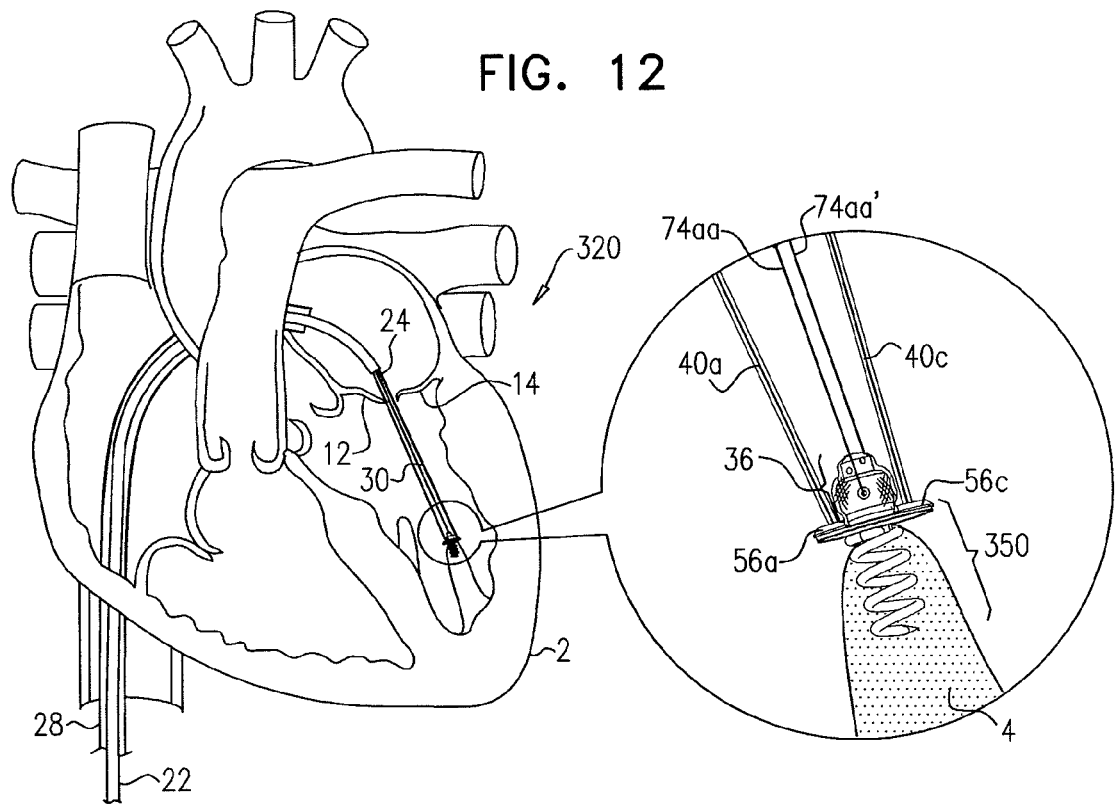
Figure 13:
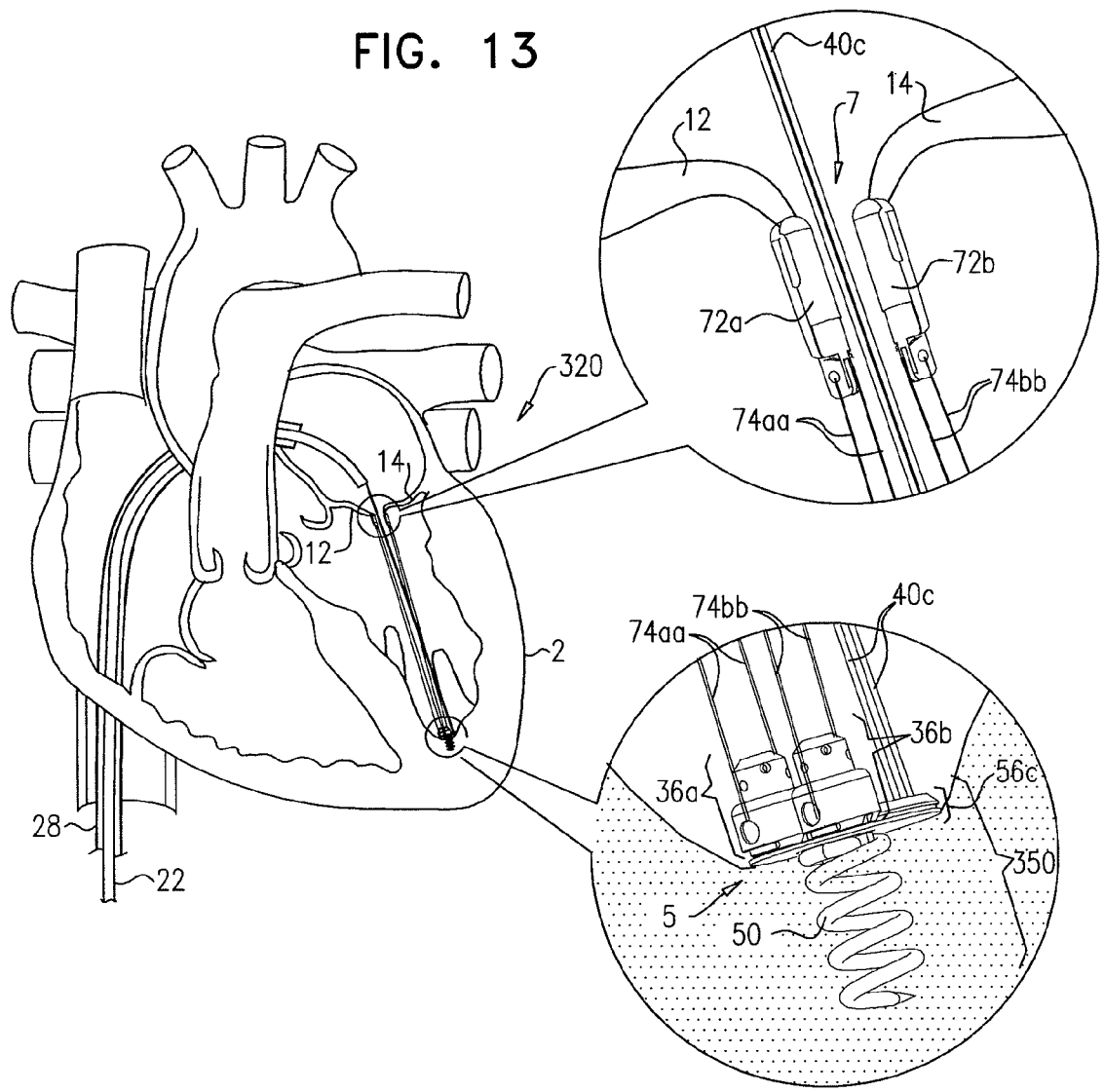
Figure 14:
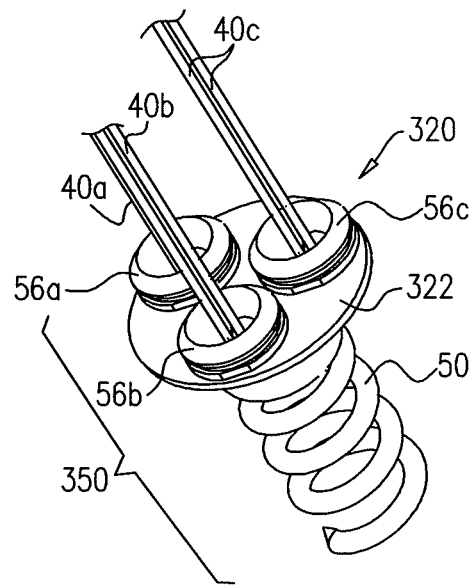

As shown in FIGS. 11-13, first and second spool assemblies 36a and 36b are coupled via guide wires 40a and 40b to respective docking stations 56a and 56b. Each spool assembly 36a and 36b has a respective chord 74aa and 74bb extending therefrom. For example, the chord extending from spool assembly 36a has portions 74aa and 74aa' extending from spool assembly 36a. Each chord 74 is coupled to a respective leaflet-engaging element 72. That is, chord 74aa is coupled to leaflet-engaging element 72a, and chord 74bb is coupled to leaflet-engaging element 72b. Each leaflet-engaging element 72a and 72b is coupled to leaflets 12 and 14, respectively, and each spool assembly 36a and 36b is coupled to respective docking stations 56a and 56b, as described hereinabove (FIG. 13). Chords 74aa and 74bb are then adjusted, as described hereinabove. Each chord 74aa and 74bb may be adjusted sequentially or simultaneously.

FIG. 13 shows chords 74aa and 74bb following their adjustment. The relative dispositions of leaflets 12 and 14 are adjusted in conjunction with the adjusting of chords 74aa and 74bb. Typically, leaflets 12 and 14 are drawn together.

Figure 15:
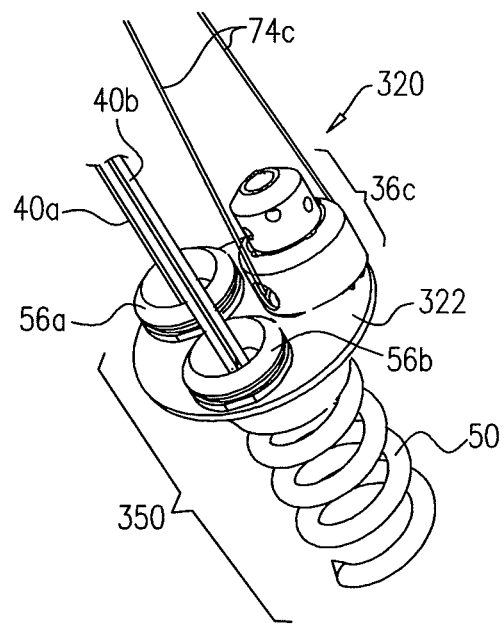

As shown in FIG. 15, a third spool assembly may be coupled to docking station 56c. Chord 74c coupled thereto may be coupled to a third implantation site in heart 2 and subsequently adjusted. FIG. 15 shows third spool assembly 36c coupled to docking station 56c without the presence of the other spool assemblies 36a and 36b, by way of illustration and not limitation.

Figure 16:
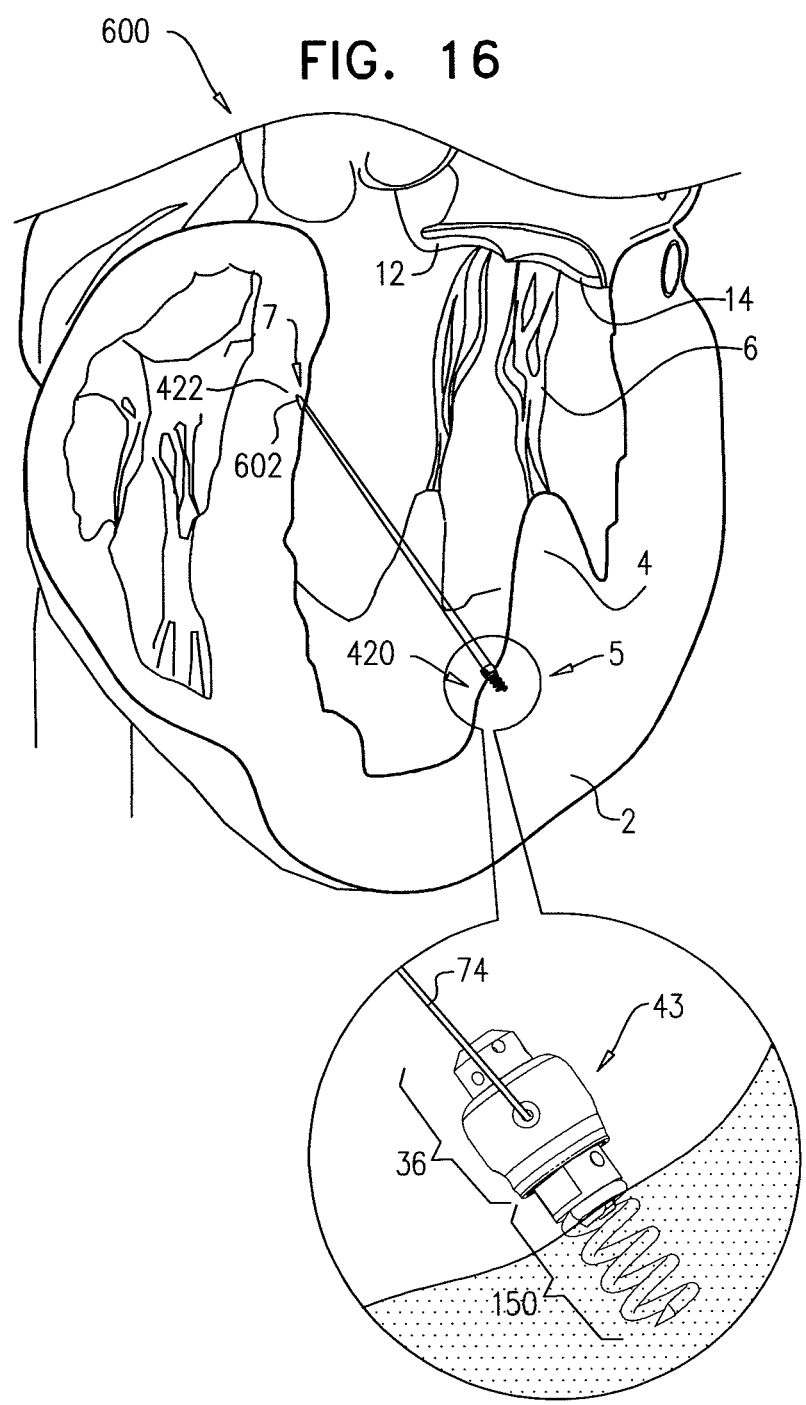
FIG. 16 is a schematic illustration of wall-to-wall adjustment using the docking station, adjustment mechanism, and repair chord, in accordance with some applications of the present invention.

FIG. 16 shows a system 600 for repairing malpositioning of the wall of the ventricle of the patient, in accordance with respective applications of the present invention. System 600 treats a weakened state in which the wall of the left ventricle is malpositioned and weakened. As a result, leaflets 12 and 14 of mitral valve 8 are malpositioned and are distanced from one another. Spool assembly 36 implanted at a first portion 420 of heart tissue which faces and surrounds the left ventricle of heart 2. First implantation site 5 thus comprises first portion 420 of heart tissue. It is to be noted that first implantation site 5 is at the base of the papillary muscle by way of illustration and not limitation, and that first implantation site 5 may be at a portion of the wall of the heart in a vicinity of the apex of the heart, or at papillary muscle 4.

Spool assembly 36 is implanted via docking assembly 150 at site 5 in a manner as described hereinabove with reference. The free ends of chord 74 are coupled to a second portion 422 of heart tissue which faces and surrounds the left ventricle of heart 2. Second implantation site 7 thus comprises second portion 422 of heart tissue, e.g., at the septum, by way of illustration and not limitation. The free ends of longitudinal chord 74 are coupled to the heart tissue using any suitable attachment means 602, e.g., sutures, knotting, or tissue anchors such as helical anchors. Spool 46 of adjustment mechanism 43 is rotated, as described hereinabove, thereby pulling tight chord 74 and thereby reducing a length of chord 74 between first and second implantation sites 5 and 7. In response to the pulling of chord 74, first and second portions 420 and 422 of the heart tissue are pulled toward one another, and a length of chord 74 is adjusted. Consequently, the dimensions of the heart wall are restored to physiological dimensions, and leaflets 12 and 14 are drawn toward one another.

Figure 17:
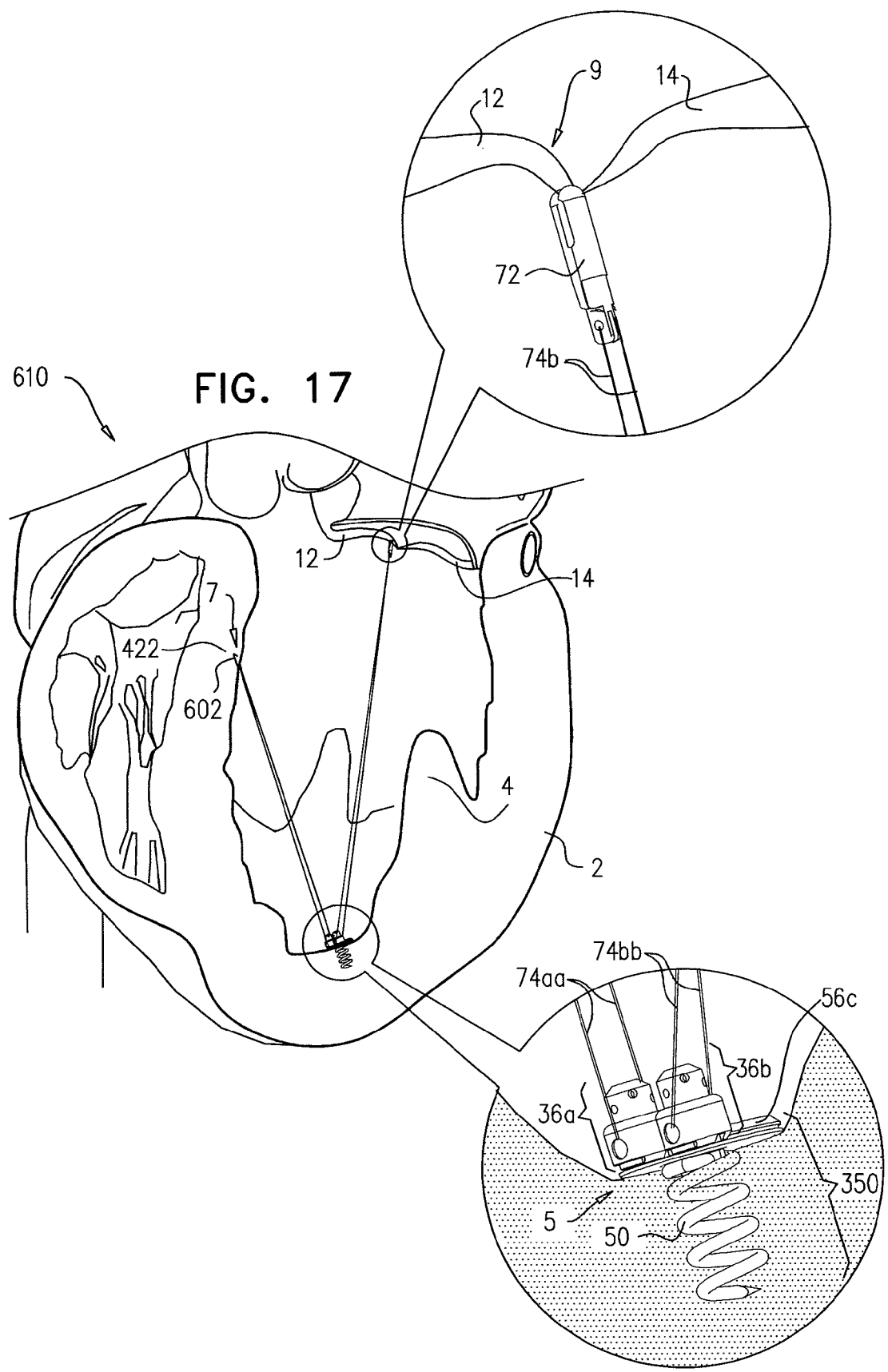
FIG. 17 is a schematic illustration of wall-to-wall adjustment and leaflet adjustment using the plurality of docking stations, the plurality of adjustment mechanisms, and the plurality of repair chords, in accordance with some applications of the present invention.

FIG. 17 shows a system 610 for adjusting both malpositioning of a heart wall of heart 2, and a relative disposition of leaflet 12, in accordance with some applications of the present invention. Multiple-docking-station assembly 350 is implanted at implantation site 5, i.e., a portion of tissue of a heart wall of heart 2 in a vicinity of the apex of heart 2. It is to be noted that implantation site 5 may include any portion of tissue of heart 2, e.g., a portion of tissue at the base of papillary muscle 4, a portion of tissue of papillary muscle 4, or a portion of the free wall of the ventricle. As described hereinabove, first spool assembly 36a is coupled to docking station 56a and adjusts a length of chord 74aa in order to adjust a distance between implantation sites 5 and 7. Second spool assembly 36b is coupled to docking station 56b and adjusts a length of chord 74bb in order to adjust a distance between implantation site 5 a third implantation site 9 (e.g., leaflet 12, as shown). As described hereinabove, chords 74aa and 74bb may be adjusted simultaneously or sequentially. Following the adjusting implantation sites 7 and 9 are drawn toward multiple-docking-station assembly 350 at implantation site 5. Consequently, the dimensions of the heart wall are restored to physiological dimensions, and leaflets 12 and 14 are drawn toward one another.

Figure 18:
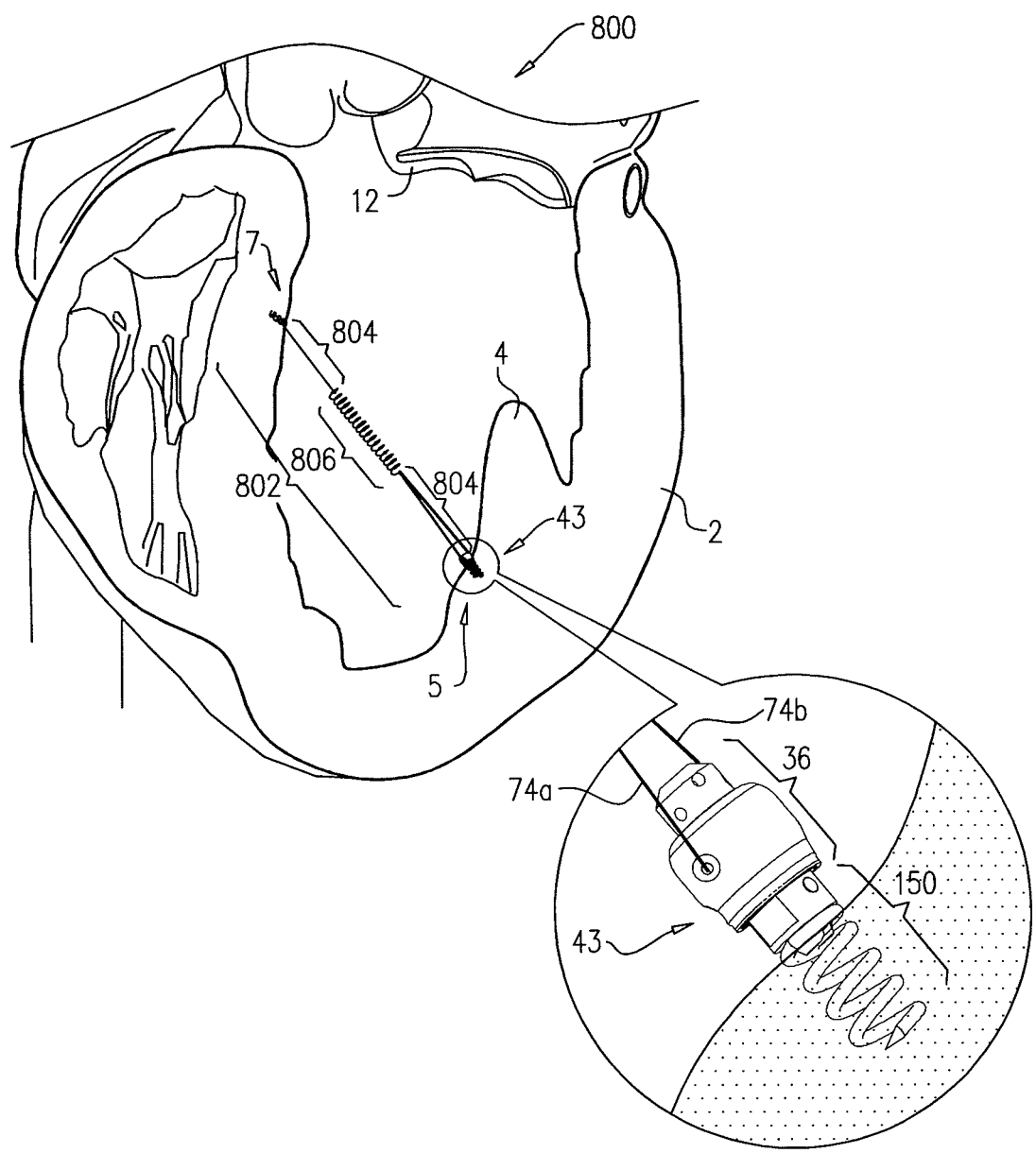
FIG. 18 is a schematic illustration of wall-to-wall adjustment using the docking station, adjustment mechanism, and repair chord, in accordance with some other applications of the present invention.

FIG. 18 is a schematic illustration of a system 800 for adjusting a distance between two portions of a heart wall of the left ventricle of the patient, in accordance with some applications of the present invention. System 800 comprises a tensioning device 802 coupled at a first end thereof to spool assembly 36 at docking assembly 150. In a manner as described hereinabove, spool assembly 36 is implanted at first implantation site 5 in a first portion of tissue of the heart wall that faces and surrounds the ventricular lumen. The free end of tensioning device 802 is attached at second implantation site 7 to a second portion of tissue of the heart wall that faces and surrounds the ventricular lumen. The free end of tensioning device 802 is implanted in heart tissue using a helical anchor by way of illustration and not limitation. For example, the free end of tensioning device 802 may be coupled to second implantation site 7 using sutures, knots, or any tissue anchor known in the art.

Tensioning device 802 comprises a flexible material, e.g., ePTFE or nitinol, and is shaped to define a coiled portion 806 that has a length of between 20 mm and 50 mm and a diameter of between 0.5 mm and 3.0 mm. Tensioning device 802 comprises wire/suture portions 804 on either side of coiled portion 806.

As described hereinabove, spool 46 of adjustment mechanism 43 is rotated in order to adjust a distance between first and second implantation sites 5 and 7. As spool 46 is rotated in a first direction thereof, suture portion 804 that is disposed adjacently to spool assembly 36 is wrapped around spool 46. Tensioning device 802 is tightened and shortened in response to the wrapping of portion 804 around spool 46. As device 802 is tightened, a force is applied to coiled portion 806 of tensioning device 802. Coiled portion 806 applies a supplemental puling force to help pull the opposing first and second portions of the ventricle wall toward one another. Consequently, the dimensions of the heart wall are restored to physiological dimensions, and leaflets 12 and 14 are drawn toward one another.

Reference is made to FIGS. 16-18. It is to be noted that the scope of the present invention includes the use of systems 600, 610, and 800 for adjusting a distance between any two portions of the heart and not just opposing portions, as described hereinabove. For example, first and second implantation sites 5 and 7 may be on the same side, e.g., the septum, of the wall of the heart.

Figure 19:
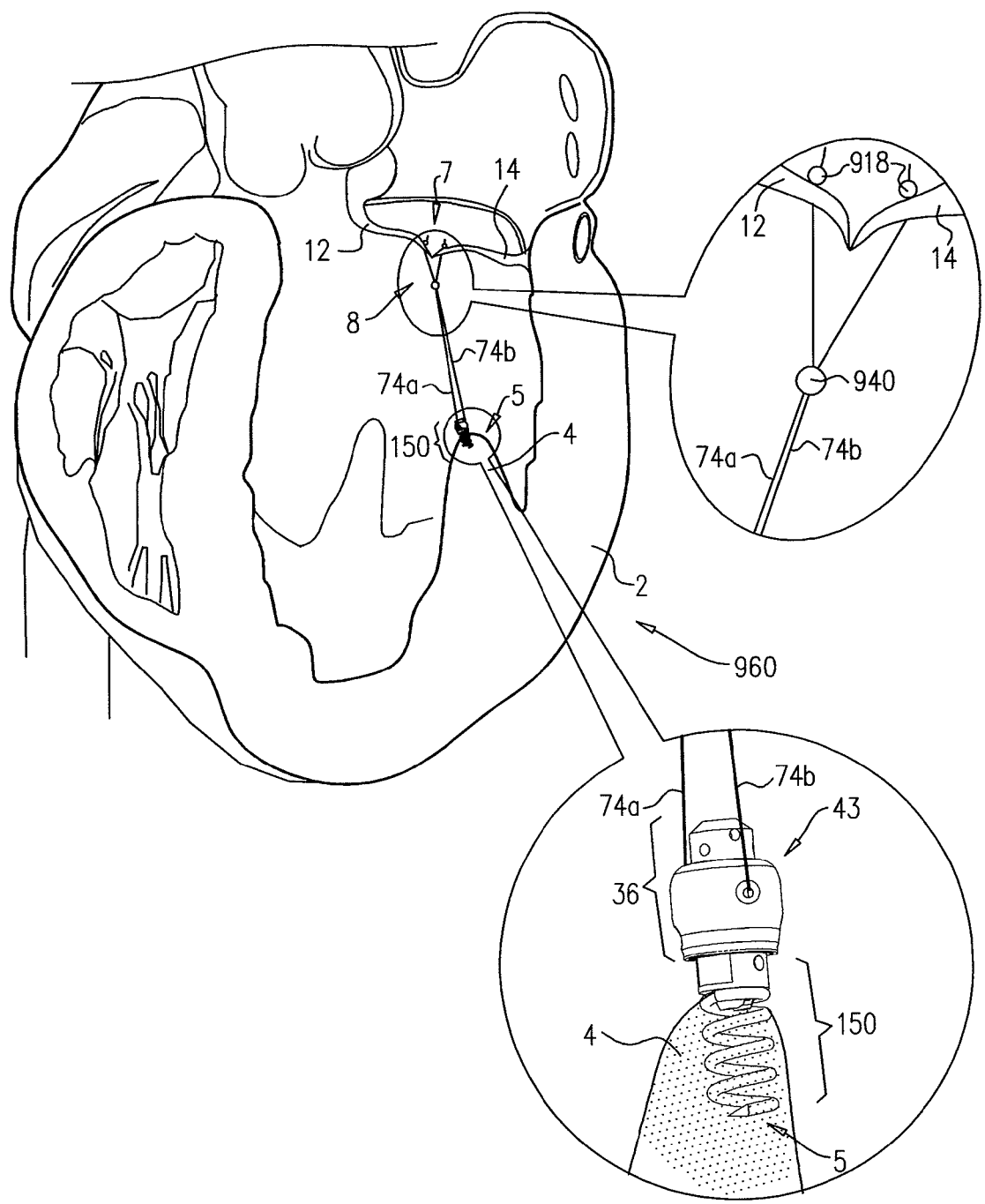
FIGS. 19-20 are schematic illustrations of adjustment of a valve of a patient from a middle portion of the valve, in accordance with some applications of the present invention.

Reference is now made to FIG. 19 which is a schematic illustration of a system 960 for drawing together leaflets 12 and 14 of mitral valve 8 of the patient, in accordance with some applications of the present invention. Spool assembly 36 is implanted via docking assembly 150 in first implantation site 5 at papillary muscle 4 of the left ventricle by way of illustration and not limitation. For example, spool assembly 36 may be implanted in a portion of the heart wall of the ventricle, e.g., the base of the papillary muscle. First and second portions 74a and 74b of chord 74 are coupled, e.g., sutured, anchored, clipped, locked in place with a crimping bead 918, to leaflet 12 at an implantation site 902. It is to be noted that portions 74a and 74b may be coupled to leaflets 12 and 14, respectively, using leaflet-engaging elements 72 as described hereinabove.

As described hereinabove, spool 46 of adjustment mechanism 43 is rotated in order to adjust a length of portions 74a and 74b of chord 74. Portions 74a and 74b are pulled tight in response to rotation of spool 46 in a first direction thereof. In response to the pulling of portions 74a and 74b, leaflets 12 and 14 are pulled toward one another in order to restore coaptation to valve 8.

It is to be noted that system 960 may be used on the tricuspid valve.

System 960 further comprises at least one bead 940 that is threaded over portions 74a and 74b of chord 74. The surgeon adjusts the position of the bead along the portions 74a and 74b in order to set the degree to which portions 74a and 74b are free to move with respect to one another. In general, as the bead is positioned closer to the valve, the portions 74a and 74*b* are more constrained in their motion with respect to one another, and the leaflets are drawn closer together. For some applications of the present invention, the bead comprises a fixation mechanism (e.g., a crimping mechanism), which is configured to fix the bead to the longitudinal members once the bead has been positioned at a desire location along the members.

Figure 20:
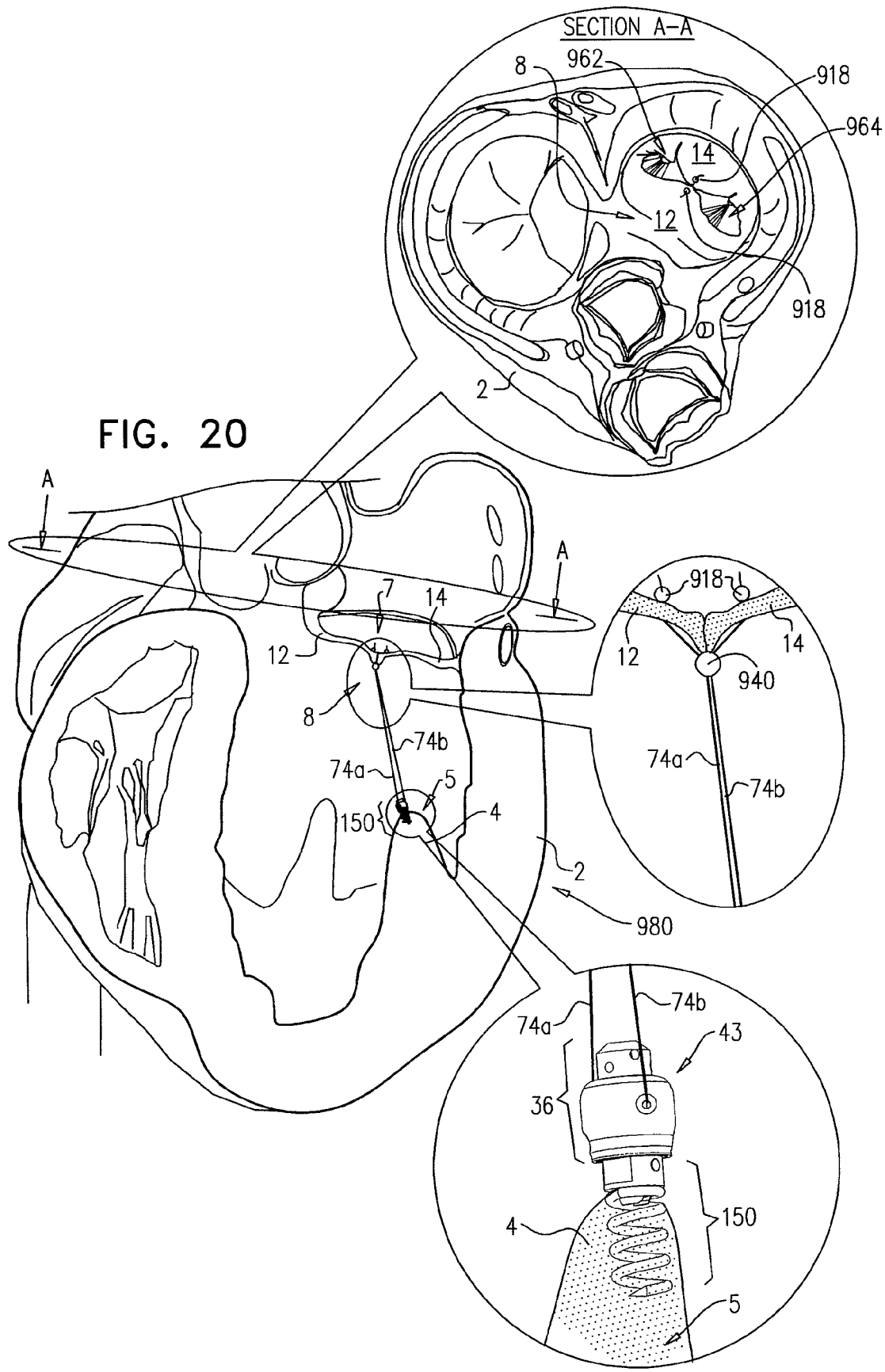

FIG. 20 shows a system 980 that is similar to system 960 as described with reference to FIG. 19, with the exception that bead 940 is pulled by the operating physician to the ventricular surface of a middle portion of valve 8, in accordance with some applications of the present invention. Such pulling of bead 940 to the ventricular surface creates a bridge between leaflets 12 and 14, e.g., as an Alfieri stitch, or edge-to-edge repair. Portions 74*a* and 74*b* are then adjusted in order to pull together the middle portion of mitral valve 8, as shown in Section A-A. The firm coupling of leaflets 12 and 14 prevents prolapsing of leaflets 12 and 14, facilitates coaptation of leaflets 12 and 14, and creates orifices 962 and 964 in mitral valve 8 so as to facilitate blood flow from the atrium to the ventricle. Additionally, the adjusting of portions 74*a* and 74*b* of chord 74 draws downward leaflets 12 and 14 and adjusts chord 74 such that it functions as an artificial chordea tendinea.

Reference is now made to FIGS. 19 and 20. It is to be noted that although docking assembly 150 is shown, multiple-docking-station assembly 350 as described hereinabove, may be implanted at implantation site 5. For such an application, two or more spool assemblies 36 may be coupled to multiple-docking-station assembly 350, and any number of chords 74 extending from each spool assembly 36 may be coupled to leaflets 12 and 14 at any suitable location thereof. The lengths of chords 74 are then adjusted by spool assemblies 36 in order to pull leaflets 12 and 14 together.

For some applications of the present invention, systems 20, 220, 320, 600, 610, 800, 960, and 980 are used to treat an atrioventricular valve other than the mitral valve, i.e., the tricuspid valve. For these applications, systems 20, 220, 320, 600, 610, 800, 960, and 980 described hereinabove as being placed in the left ventricle are instead placed in the right ventricle.

For some applications, techniques described herein are practiced in combination with techniques described in one or more of the references cited in the Background section of the present patent application.

Additionally, the scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

U.S. patent application Ser. No. 11/950,930 to Gross et al., entitled, "Segmented ring placement," filed on Dec. 5, 2007, which published as U.S. Patent Application Publication 2008/0262609;

U.S. patent application Ser. No. 12/341,960 to Cabiri, entitled, "Adjustable partial annuloplasty ring and mechanism therefor," filed on Dec. 22, 2008, which published as U.S. Patent Application Publication 2010/0161047, and which issued as U.S. Pat. No. 8,241,351;

U.S. patent application Ser. No. 12/435,291 to Maisano et al., entitled, "Adjustable repair chords and spool mechanism therefor," filed on May 4, 2009, which published as U.S. Patent Application Publication 2010/0161041, and which issued as U.S. Pat. No. 8,147,542;

U.S. patent application Ser. No. 12/437,103 to Zipory et al., entitled, "Annuloplasty ring with intra-ring anchoring," filed on May 7, 2009, which published as U.S. Patent Application Publication 2010/0286767;

PCT Publication WO 10/004,546 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Aug. 27, 2009, which published as U.S. Patent Application Publication 2010/0161042;

U.S. patent application Ser. No. 12/608,316 to Miller et al., entitled, "Tissue anchor for annuloplasty ring," filed on Oct. 29, 2009, which published as US Patent Application Publication 2011/0106247, and which issued as U.S. Pat. No. 8,277,502;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009;

U.S. patent application Ser. No. 12/689,635 to Zipory et al., entitled, "Over-wire rotation tool," filed on Jan. 19, 2010, which published as US Patent Application Publication 2010/0280604;

U.S. patent application Ser. No. 12/689,693 to Hammer et al., entitled, "Application Deployment techniques for annuloplasty ring," filed on Jan. 19, 2010, which published as US Patent Application Publication 2010/0280605;

U.S. patent application Ser. No. 12/706,868 to Miller et al., entitled, "Actively-engageable movement-restriction mechanism for use with an annuloplasty structure," filed on Feb. 17, 2010, which published as US Patent Application Publication 2010/0211166, and which issued as U.S. Pat. No. 8,353,956;

PCT Patent Application PCT/IL2010/000357 to Maisano et al., entitled, "Implantation of repair chords in the heart," filed on May 4, 2010, which published as PCT Publication WO 2010/128502;

PCT Patent Application PCT/IL2010/000358 to Zipory et al., entitled, "Deployment techniques for annuloplasty ring and over-wire rotation tool," filed on May 4, 2010, which published as PCT Publication WO 2010/128503; and/or U.S. Regular application Ser. No. 12/785,717 to Miller et al., entitled, "Adjustable artificial chordeae tendineae with suture loops," filed on May 24, 2010, which published as US Patent Application Publication 2011/0288635.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
coupling a tissue-engaging element to a first portion of cardiac tissue of a heart of a patient;
advancing toward the tissue-engaging element an adjustment mechanism along at least a portion of at least one guide member, a distal end of which is removably attached by a docking assembly to the tissue-engaging element, the adjustment mechanism engaging at least a first portion of at least a first flexible longitudinal member;
coupling a second portion of the first flexible longitudinal member to a second portion of cardiac tissue;
following the coupling of the second portion of the first flexible longitudinal member to the second portion of cardiac tissue:
sliding the adjustment mechanism further along the guide member; and
securing the adjustment mechanism within the heart of the patient by locking the adjustment mechanism to the tissue-engaging element;
using the adjustment mechanism, adjusting a length of the first flexible longitudinal member between the first and second portions of cardiac tissue; and
detaching the guide member from the docking assembly after the locking of the adjustment mechanism to the tissue-engaging element.

2. The method according to claim 1, wherein coupling the tissue-engaging element to the first portion of cardiac tissue comprises coupling the tissue-engaging element to a papillary muscle of a ventricle of the patient.

3. The method according to claim 1, wherein coupling the tissue-engaging element to the first portion of cardiac tissue comprises coupling the tissue-engaging element to a portion of an inner wall of a ventricle of the patient.

4. The method according to claim 1, wherein adjusting the length of the flexible longitudinal member comprises adjusting a distance between the first and second portions of cardiac tissue.

5. The method according to claim 1, wherein adjusting the length of the flexible longitudinal member comprises adjusting the length of the flexible longitudinal member during beating of the heart of the patient.

6. The method according to claim 1, wherein adjusting the length of the flexible longitudinal member comprises adjusting the length of the flexible longitudinal member during a first period thereof, and wherein the method further comprises further adjusting the length of the flexible longitudinal member during a second period that is after the first period.

7. The method according to claim 1, wherein coupling the tissue-engaging element to the first portion of cardiac tissue comprises coupling the tissue-engaging element to an intracardiac portion of tissue in a manner in which a distal portion of the tissue-engaging element does not extend beyond an epicardium of the heart of the patient.

8. The method according to claim 1, wherein coupling the second portion of the flexible longitudinal member to the second portion of cardiac tissue comprises coupling the second portion of the flexible longitudinal member to at least one leaflet of an atrioventricular valve of the patient.

9. The method according to claim 1, wherein coupling the second portion of the flexible longitudinal member to the second portion of cardiac tissue comprises coupling the second portion of the flexible longitudinal member to exactly one leaflet of an atrioventricular valve of the patient.

10. The method according to claim 1, wherein coupling the second portion of the flexible longitudinal member to the second portion of cardiac tissue comprises coupling, to a leaflet of an atrioventricular valve, a clip that is coupled to the second portion of the flexible longitudinal member.

11. The method according to claim 1, wherein locking the adjustment mechanism to the tissue-engaging element comprises locking the adjustment mechanism to a docking station coupled to the tissue-engaging element.

12. The method according to claim 1, wherein advancing the adjustment mechanism comprises transcatheterally advancing the adjustment mechanism.

13. The method according to claim 1, wherein advancing the adjustment mechanism comprises threading the guide member through an opening in the adjustment mechanism prior to the advancing.

14. The method according to claim 1, further comprising:
advancing a first portion of a second flexible longitudinal member, toward the tissue-engaging element; and
coupling a second portion of the second flexible longitudinal member to a third portion of cardiac tissue.

15. The method according to claim 14, further comprising coupling the first portion of the second flexible longitudinal member to the tissue-engaging element following the coupling of the second portion of the second flexible longitudinal member to the third portion of cardiac tissue.

16. The method according to claim 14, wherein:
the second portion of cardiac tissue includes a portion of tissue of a ventricle of the patient,
coupling the second portion of the first flexible longitudinal member to the second portion of cardiac tissue comprises coupling the second portion of the first flexible longitudinal member to the portion of tissue of the ventricle of the patient,
the third portion of cardiac tissue includes at least one leaflet of an atrioventricular valve of the heart of the patient, and
coupling the second portion of the second flexible longitudinal member to the third portion of cardiac tissue comprises coupling the second portion of the second flexible longitudinal member to the at least one leaflet of the atrioventricular valve.

17. The method according to claim 1, wherein the at least one guide member comprises first and second guide members, and wherein coupling the tissue-engaging element to the first portion of tissue comprises coupling a tissue-engaging element coupled to at least first and second docking stations of the docking assembly, the first and second docking stations being removably coupled to the first and second guide members, respectively.

18. The method according to claim 17, wherein:
advancing the adjustment mechanism comprises:
advancing a first adjustment mechanism along the first guide member, the first adjustment mechanism engaging at least the first portion of at least the first flexible longitudinal member; and
coupling the first adjustment mechanism to the first docking station, and the method further comprises:
advancing a second adjustment mechanism along the second guide member, the second adjustment mechanism engaging at least a first portion of at least a second flexible longitudinal member; and
coupling the second adjustment mechanism to the second docking station.

19. The method according to claim 18, wherein the method further comprises coupling a second portion of the second flexible longitudinal member to a third portion of cardiac tissue.

20. The method according to claim 19, wherein:
the second portion of cardiac tissue includes a portion of tissue of a ventricle of the patient,
coupling the second portion of the first flexible longitudinal member to the second portion of cardiac tissue comprises coupling the second portion of the first flexible longitudinal member to the portion of tissue of the ventricle of the patient,
the third portion of cardiac tissue includes at least one leaflet of an atrioventricular valve of the heart of the patient, and
coupling the second portion of the second flexible longitudinal member to the third portion of cardiac tissue comprises coupling the second portion of the second flexible longitudinal member to the at least one leaflet of the atrioventricular valve.

21. The method according to claim 1, wherein coupling the second portion of the first flexible longitudinal member to the second portion of cardiac tissue comprises coupling the second portion of the first flexible longitudinal member to a portion of a wall of a ventricle of the patient, and wherein adjusting the length of the flexible member.

22. The method according to claim 21, wherein adjusting the distance between the portion of the wall and the first portion of cardiac tissue comprises adjusting a heart wall malpositioning of the patient.

23. The method according to claim 1, wherein the adjustment mechanism includes a spool coupled to the first portion of the first flexible longitudinal member, and wherein adjusting the length of the first flexible longitudinal member using the adjustment mechanism comprises rotating the spool.

24. The method according to claim 23, further comprising unwinding a portion of the first flexible longitudinal member from around the spool, and wherein adjusting the length of the first flexible longitudinal member comprises applying tension to the first flexible longitudinal member subsequently to the unwinding.

25. The method according to claim 23, wherein adjusting the length of the first flexible longitudinal member comprises:
applying tension to the first flexible longitudinal member by winding successive portions of the first flexible longitudinal member around the spool by rotating the spool in a first rotational direction thereof, and
slackening the first flexible longitudinal member by unwinding the successive portions of the first flexible longitudinal member from around the spool by rotating the spool in a second rotational direction thereof opposite the first rotational direction.

26. The method according to claim 23, further comprising unlocking the spool prior to the adjusting the length of the first flexible longitudinal member, and locking the spool following the adjusting the length of the first flexible longitudinal member.

27. The method according to claim 1, wherein:
the second portion of tissue includes at least one leaflet of an atrioventricular valve of the patient,
the first flexible longitudinal member comprises an artificial chordea tendinea, and locking the adjustment mechanism to the tissue-engaging element comprises:
advancing, between leaflets of the atrioventricular valve and into the ventricle, at least one shaft of a delivery tool, to which shaft the adjustment mechanism is removably coupled; and
while the shaft remains coupled to the adjustment mechanism, coupling, using a coupling element holder of the delivery tool, at least one leaflet-engaging element to the at least one leaflet, wherein the second portion of the artificial chordea tendinea is coupled to the at least one leaflet-engaging element.

28. The method according to claim 27, wherein advancing the at least one shaft comprises transcatheterally advancing the at least one shaft.

29. The method according to claim 27, wherein coupling the at least one leaflet-engaging element to the at least one leaflet comprises coupling the at least one leaflet-engaging element to exactly one leaflet.

30. The method according to claim 27, wherein using the coupling element holder of the delivery tool comprises sliding the coupling element holder with respect to the guide member.

31. The method according to claim 1, wherein:
the first flexible longitudinal member includes first and second cord portions thereof, each of the first and second cord portions having respective free ends,
the first and second cord portions of the first flexible longitudinal member extend from the adjustment mechanism, and
coupling the second portion of the first flexible longitudinal member to the second portion of cardiac tissue comprises coupling each free end of the first and second cord portions to respective first and second leaflets of an atrioventricular valve of the patient.

32. The method according to claim 31, wherein adjusting the length of the first flexible longitudinal member comprises:
adjusting a length of the first cord portion of the first flexible longitudinal member between the adjustment mechanism and the first leaflet;
adjusting a length of the second cord portion of the first flexible longitudinal member between the adjustment mechanism and the second leaflet; and
by the adjusting the lengths of the first and second cord portions of the first flexible longitudinal member, drawing together the first and second leaflets.

33. The method according to claim 32, wherein drawing together comprises drawing together the first and second leaflets using a bead through which the first and second cord portions of the first longitudinal member pass.

34. The method according to claim 33, wherein using the bead comprises advancing the bead to ventricular surfaces of the first and second leaflets, and wherein advancing the bead to the ventricular surfaces comprises creating an edge-to-edge repair of the first and second leaflets.

35. The method according to claim 1, wherein locking the adjustment mechanism to the tissue-engaging element comprises securing the first portion of the first flexible longitudinal member to the first portion of cardiac tissue by locking the adjustment mechanism to the tissue-engaging element.

36. The method according to claim 1, wherein coupling the second portion of the first longitudinal member to the second portion of cardiac tissue comprises coupling the second portion of the first flexible longitudinal member to the second portion of cardiac tissue by securing, to the second portion of cardiac tissue, a second tissue-engaging element that is removably coupled to the guide member.

37. The method according to claim 1, wherein sliding the adjustment mechanism further along the guide member comprises sliding the adjustment mechanism further along the guide member, toward the tissue-engaging element, and away from the second portion of the first flexible longitudinal member.

38. The method according to claim 1, wherein sliding the adjustment mechanism further along the guide member comprises moving the first portion of the first flexible longitudinal member with respect to the guide member and toward the tissue-engaging element by the sliding of the adjustment mechanism further along the guide member.

39. A method comprising:
coupling a tissue-engaging element to a first portion of cardiac tissue of a heart of a patient;
advancing toward the tissue-engaging element an adjustment mechanism along at least a portion of at least one guide member that is removably attached to the tissue-engaging element, the adjustment mechanism engaging at least a first portion of at least a first flexible longitudinal member;
coupling a second portion of the first flexible longitudinal member to a second portion of cardiac tissue;
following the coupling of the second portion of the first flexible longitudinal member to the second portion of cardiac tissue:
sliding the adjustment mechanism further along the guide member; and
securing the adjustment mechanism within the heart of the patient by locking the adjustment mechanism to the tissue-engaging element; and
subsequently, using the adjustment mechanism, adjusting a length of the first flexible longitudinal member between the first and second portions of cardiac tissue.

* * * * *

UNITED STATES PATENT AND TRADEMARK OFFICE
CERTIFICATE OF CORRECTION

| | | |
|---|---|---|
| PATENT NO. | : 8,690,939 B2 | Page 1 of 1 |
| APPLICATION NO. | : 12/795192 | |
| DATED | : April 8, 2014 | |
| INVENTOR(S) | : Eran Miller and Oz Cabiri | |

It is certified that error appears in the above-identified patent and that said Letters Patent is hereby corrected as shown below:

In the Claims

Column 23, line 22, In Claim 21, before ".", insert --comprises adjusting a distance between the portion of the wall and the first portion of cardiac tissue--

Signed and Sealed this
Second Day of September, 2014

Michelle K. Lee
*Deputy Director of the United States Patent and Trademark Office*